(12) United States Patent
Strobel et al.

(10) Patent No.: US 7,259,004 B1
(45) Date of Patent: Aug. 21, 2007

(54) ENDOPHYTIC STREPTOMYCETES FROM HIGHER PLANTS WITH BIOLOGICAL ACTIVITY

(75) Inventors: Gary A. Strobel, Bozeman, MT (US); Uvidelio F. Castillo, Saukville, WI (US)

(73) Assignee: Montana State University, Bozeman, MT (US)

( * ) Notice: Subject to any disclaimer, the term of this patent is extended or adjusted under 35 U.S.C. 154(b) by 249 days.

(21) Appl. No.: 10/406,006

(22) Filed: Apr. 3, 2003

Related U.S. Application Data

(60) Provisional application No. 60/369,312, filed on Apr. 3, 2002, provisional application No. 60/407,782, filed on Sep. 3, 2002.

(51) Int. Cl.
*C12N 1/20* (2006.01)
(52) U.S. Cl. .............................. 435/252.35; 424/93.43
(58) Field of Classification Search ...................... None
See application file for complete search history.

(56) References Cited

OTHER PUBLICATIONS

Sessitsch et al., FEMS Microbiology Ecology, vol. 39 No. 1, 23-32. 2002. (First published online Dec. 5, 2001.).*
Sardi et al., Appl. Environ. Microbiol,, 1992. vol. 58, No. 8, pp. 2691-2693.*
Bieber et al., Journal of Antibiotics (Tokyo), (Mar. 1998) vol. 51, No. 3, pp. 381-382.*
Shimizu et al., J. of General Plant Pathology, vol. 66,(1) pp. 360-366.*
Shimizu et al., J. of General Plant Pathology, vol. 66,(1) pp. 360-366. 2000.*
Bieber et al., "Alnumycin a New Naphthoquinone Antibiotic Produced by an Endophytic *Streptomyces* sp.," Journal of Antibiotics (Tokyo), Mar. 1998, vol. 51, No. 3, pp. 381-382.
Sardi et al., "Isolation of Endophytic *Streptomyces* Strains from Surface-Sterilized Roots," Applied and Environmental Micobiology, 1992, vol. 58, No. 8, pp. 2691-2693.
Sessitsch et al., "Cultivation-independent population analysis of bacterial endophytes in three potato varieties based on eubacterial and *Actinomycetes*-specific PCR of 16S rRNA genes," FEMS Microbiology Ecology, 2002 (first published online Dec. 5, 2001), vol. 39, No. 1, pp. 23-32.
Shimizu et al., "Studies on Endophytic Actinomycetes (I) *Streptomyces* sp. Isolated from Rhododendron and Its Antifungal Activity," General Plant Pathology, vol. 66, pp. 360-366 (2002).

* cited by examiner

*Primary Examiner*—Irene Marx
(74) *Attorney, Agent, or Firm*—Klarquist Sparkman, LLP

(57) ABSTRACT

The present invention relates to isolated strains of a *Streptomyces* spp. which are endophytes of dicotyledonous plants and to methods for selecting such strains. The present invention also relates to compounds having biological activity selected from the group consisting of munumbicin A, munumbicin B, munumbicin C and munumbicin D, kakadumycin A, kakadumycin B, and kakadumycin C. The present invention further relates to compositions of such compounds and to methods of protecting plants against attack by a plant pathogen and methods of inhibiting bacterial growth, fungal growth, viral infection, growth of parasitic organisms, and cancer cell growth with such compositions.

6 Claims, 16 Drawing Sheets

¹H spectrum of kakadumycin in CDCl₃

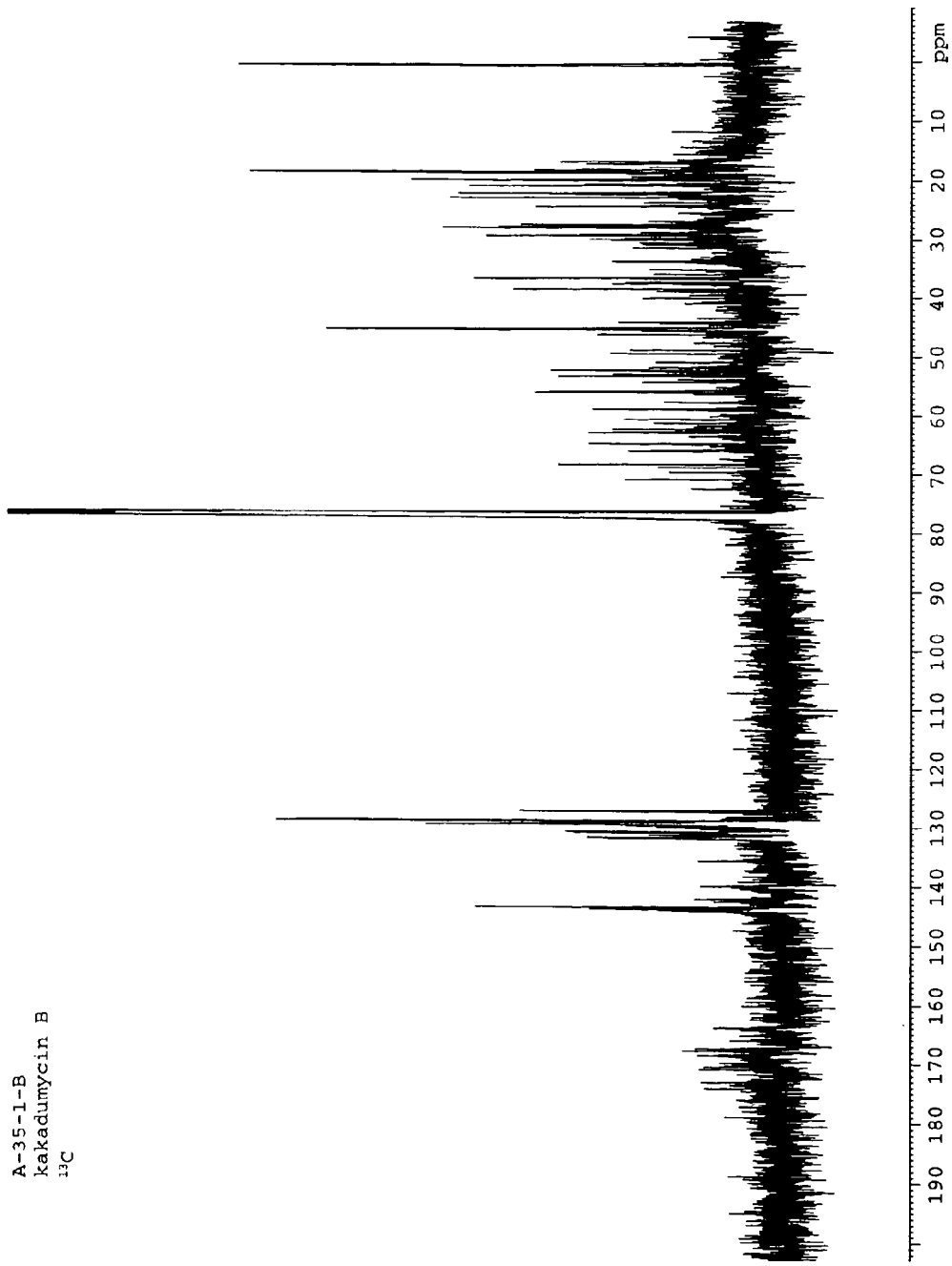

ENDOPHYTIC STREPTOMYCETES FROM HIGHER PLANTS WITH BIOLOGICAL ACTIVITY

CROSS-REFERENCE TO RELATED APPLICATIONS

This application claims the benefit of U.S. Provisional Application No. 60/369,312, filed Apr. 3, 2002, and U.S. Provisional Application No. 60/407,782, filed Sep. 3, 2002, which applications are incorporated herein by reference.

STATEMENT OF RIGHTS TO INVENTIONS MADE UNDER FEDERALLY SPONSORED RESEARCH

This invention was partially made with government support under grant number GM08521-40 from the National Institutes of Health (NIH). The U.S. Government has certain rights in this invention.

BACKGROUND OF THE INVENTION

1. Field of the Invention

The present invention relates to endophytic Streptomycetes from higher plants having desirable biological activities. The present invention also relates to extracts and compounds obtainable from such strains demonstrating the desirable biological activities, including the munumbicin and kakadumycin compounds, and related families of biologically active compounds, are also provided. The present invention further relates to compositions comprising the extracts and compounds as well as methods of using the compositions.

2. Description of the Related Art

The bacterial order Actinomycetales includes several genera of bacteria similar to fungi in that they have a branching, filamentous structure. The branching filaments of the Actinomycetes eventually develop a network of strands called mycelium, which are similar in appearance to the mycelium of some fungi. Actinomycetes also form spores.

Actinomycetes are particularly valued for the property of producing antibiotics, with the most productive genus in this group being *Streptomyces*. Over 50 commercially important antibiotics have been isolated from *Streptomyces* spp., including streptomycin, neomycin, chloramphenicol and tetracyclines. Streptomycetes are found worldwide, and are a particularly significant as members of the soil microflora. Streptomycetes are also metabolically diverse, however, and are found in a great variety of ecological environments.

Actinomycetes, in general, are not reported to be endophytes on higher plants, though recently a *Streptomyces* sp. was reported on an annual plant—*Lolium perenne* (Guerny and Mantle, 1993). This *lolium* endophyte produces a weak antibiotic designated as methylalbonoursin, which is a diketopiperazine, condensed from leucine and phenylalanine. Streptomycetes which are used as a source of biologically active compounds, such as antibiotics, have all been isolated from soil.

The development of drug resistance in human pathogenic bacteria, such as *Staphylococcus, Mycobacterium, Streptococcus, Enterococcus* and others, places an ever increasing importance on the search for new antibiotics, as diseases caused by such bacteria represent a clear and growing threat to world health (NIH, 2001). For instance, tuberculosis is the second leading cause of death in the world, killing approximately 2.5 million people per year. Up to 30% of the world's peoples are carriers of this pathogen (NIH, 2001). The incidence of tuberculosis is rising in the world's population, in part due to the increased incidence of patients with HIV/AIDS, but also due to the development of drug resistance in strains of *M. tuberculosis* (Raviglione et al, 1995; Pablosmendez et al., 1997).

In addition to the problems of drug resistance in pathogenic bacteria there is also a need for more and better antimycotics, as the human population is developing more fungal infections. This is particularly an issue with HIV/AIDS patients, but also a concern with patients with organ-transplants, who must take immunosuppressive drugs to maintain continuity of the transplanted organ. In both cases, patients with these difficulties have immune systems that are weakened. Antifungal agents that are currently available, such as amphotericin B, are toxic, and often ineffective (Walsh, 1992; Walsh and Finberg, 1999; Tiphine et al., 1999).

The increased incidence of parasitic protozoan infections is a further cause of concern. The most important of these is malaria caused by *Plasmodium* spp. that kills up to 1.5-3 million people and produces up to nearly 500 million cases per year (NIH, 2001). It is estimated that nearly 40% of the world's population is at risk of becoming infected with malaria. Global warming as well as "airport malaria" are factors contributing to the increasing spread of this disease. Another factor contributing to the increased threat of death caused by malaria is the development of drug resistance in the *Plasmodium* spp. populations (NIH, 2001). In some cases, treatment of malaria and other infectious diseases has been possible with the availability of antibiotics originally derived from soil-born *Streptomyces* spp. (Waksman, 1967; Waksman and Lechevalier 1953; and Arai, 1976).

There is also a need for environmentally sound ways to grow the world's food, and new methods of controlling pests and pathogens are continuously needed in this field, as well (Overton et al., 1996). In the past, the major source of pesticidal agents came from organic synthesis. Recently, interest has increased for using more environmentally friendly methods in agricultural production, including naturally-occurring biological compounds.

It is an object of the present invention to provide endophytic streptomycetes from higher plants, and extracts and compounds thereof, with biological activity.

REFERENCES

Arai, T. (1976). Actinomycetes: The Boundary Microorganisms. Toppan Co. Ltd, Singapore.

Bacon, C. W., and White, J. F. (2000). Microbial Endophytes. Marcel Deker Inc., N.Y.

Ballio, A., Bossa, F., DiGiogio, P., Ferranti, P., Paci, M., Pucci, P., Scaloni, A., Segre, A. and Strobel, G. A. (1994). Structure of the pseudomycins, new lipodepsipeptides produced by *Pseudomonas syringae* MSU 16H. *FEBS Letters* 355, 96-100.

Castillo, U. F., Strobel, G. A., Ford, E. J., Hess, W. M., Porter, H., Jensen, J. B., Albert, H., Robison, R., Condron, M. A. M., Teplow, D. B., Stevens, D., and Yaver, D. (2002) Munumbicins, wide spectrum antibiotics produced by *Streptomyces munumbi* endophytic on *Kennedia nigriscans. Microbiology* 148, 2675-2685.

Goodfellow, M., Williams, S.T., and Mordarski, M. (1988). Actinomycetes in Biotechnology. Academic Press, London.

Isenberg, H. D. ed. (1992). Clinical Microbiology Procedures Handbook Vol. 1, Amer. Soc. Microbiol, Washington D.C.

Miller, C. M., Miller, R. V., Garton-Kinney, D., Redgrave, B., Sears, J., Condron, M., Teplow, D. and Strobel, G. A. (1998). Ecomycins, unique antimycotics from *Pseudomonas viridiflava*. *J. Applied Microbiology*. 4, 937-944.

NIH (2001). NIAID Global Health Research Plan for HIV/AIDS, Malaria and Tuberculosis. U.S. Department of Health and Human Services. Bethesda, Md.

Overton, J. (1996). Ecologically Based Pest Mangement—New Solutions for a New Century Natl. Aca. Press. Washington D.C.

Pablosmendez, A., Raviglione, M. C., Laszlo, A., Binkin, N., Rieder, H. L., Bustreo, F., Cohn, D. L., Lambregts-vanweezenbeek, C. S. B., Kim, S. J., Chaulet, P., and Nunn, P. (1997). Global surveillance for antituberculosis-drug resistance. *New England J. Med*. 338, 1641-1649.

Raviglione, M. C., Snider, D. E., and Kochi, A. (1995). Global epidemiology of tuberculosis morbidity and mortality of a worldwide epidemic. *J. Amer. Med. Assoc*. 273, 220-226.

Sato, K., Shiratori, O., and Katagiri, K. (1967). The mode of action of quinoxaline antibiotics. Interaction of quinomycin A with deoxyribonucleic acid. *J. Antibiot*. (*Tokyo*) 20, 270-276.

Selva, E., Beretta, G., Montanini, N., Saddler, G. S., Gastaldo, L., Ferrari, P., Lorenzetti, R., Landini, P., Ripamonti, F., Goldstein, B. P., M. Berti, L. Montanaro, and M. Denaro. (1991). Antibiotic GE2270 a: a novel inhibitor of bacterial protein synthesis. I. Isolation and characterization. *J. Antibiot* (*Tokyo*) 44, 693-701.

Silverstein, R. M., Bassler, G. C., and Morrill, T. C. (1991). Spectrometric Identification of Organic Compounds. Wiley and Sons, N.Y.

Singh, M. P., Petersen, P. J., Weiss, W. J., Kong, F., and Greenstein, M. (2000). Saccharomicins, novel heptadecaglycoside antibiotics produced by Saccharothrix espanaensis: antibacterial and mechanistic activities. Antimicrob. Agents Chemother. 44, 2154-2159.

Strobel, G. A., Miller, R. V., Miller, C., Condron, M., Teplow, D. B., and Hess, W. M. (1999). Cryptocandin, a potent antimycotic from the endophytic fungus *Cryptosporiopsis cf. quercina*. *Microbiol*. 145, 1919-1926.

Strobel, G. A., Torczynski, R., and Bollon, A. (1997). *Acremonium* sp.—a leucinostatin A producing endophyte of European yew (*Taxus baccata*). *Plant Sci*. 128, 97-108.

Trager, W., and Jensen, J. B. (1976). Human malaria parasites in continuous culture. *Science* 193, 673-675.

Trager, W., and F, J. B. (1978). Cultivation of malarial parasites. *Nature* 273, 621-622.

Waksman, S. A. and Lechevalier, H. A. (1953). Actinomycetes and Their Antibiotics. Williams and Wilkins Co., Baltimore.

Waksman, S. A. (1967). The Actinomycetes. Ronald Press Co. New York.

Walsh, T. A., (1992). Inhibitors of β-glucan synthesis. In "Emerging Targets in Antibacterial and Antifungal Chemotherapy" pp. 349-373. Ed. J. A. Sutcliffe and N. H. Georgopapadakou. London: Chapman and Hall.

Walsh, T. A., and Finberg, R. W. (1999). Liposomal amphoteracin B for therapy in patients with persistent fever and neutropenia. *New England J. Med*. 340, 764-771.

Waring, M. J., and Wakelin, L. P. G. (1974). Echinomycin: a bifunctional intercalating antibiotic. *Nature* 252, 653-657.

Young, D. H., Michelotti, E. J., Sivendell, C. S., and Krauss, N. E. (1992). Antifungal properties of taxol and various analogues. *Experientia* 48, 882-885.

Zhang, Y. Z., Sun, X., Zeckner, D., Sachs, B., Current, W., and Chen, S. H. (2001a). 8-Amido-bearing pseudomycin B (PSB) analogue: novel antifungal agents. *Bioorg. Med. Chem. Lett*. 11, 123-126.

Zhang, Y. Z., Sun, X., Zeckner, D., Sachs, B., Current, W., Gidda, J., Rodriguez, M., and Chen, S. H. (2001b). Synthesis and antifungal activities of novel 3-amido bearing pseudomycin analogs. *Bioorg. Med. Chem. Lett*. 11, 903-907.

SUMMARY OF THE INVENTION

The present invention relates to isolated strains of a *Streptomyces* spp. which are endophytes of dicotyledonous plants. In a preferred embodiment, the isolated strain is selected from the group consisting of any one of the *Streptomyces* spp. of NRRL 30562, NRRL 30563, NRRL 30564, NRRL 30565, NRRL 30566, and NRRL 30567.

The present invention also relates to methods for selecting a strain of endophytic *Streptomyces* spp. having a biological activity of interest, the method comprising the steps of (a) culturing tissue from the interior region of a dicotyledonous plant on nutrient media for a time sufficient to permit colony formation by a strain of endophytic *Streptomyces* spp. associated with the tissue; and (b) selecting a *Streptomyces* spp. strain demonstrating the biological activity of interest. The present invention also relates to strains of *Streptomyces* spp. selected by such a method and to extracts thereof.

The present invention also relates to compounds having biological activity selected from the group consisting of munumbicin A, munumbicin B, munumbicin C and munumbicin D, kakadumycin A, kakadumycin B, and kakadumycin C. The present invention further relates to compositions of such compounds.

The present invention also relates to methods of protecting plants against attack by a plant pathogen and methods of inhibiting bacterial growth, fungal growth, viral infection, growth of parasitic organisms, and cancer cell growth.

BRIEF DESCRIPTION OF THE DRAWINGS

FIG. 16 shows the $^{13}$C NMR spectrum of kakadumycin B (CDCl$_3$, 500 MHz).

DETAILED DESCRIPTION OF THE INVENTION

Isolated Endophytic Microorganisms

Figure 1:
FIG. 1 shows the snakevine plant growing wild in the Northern Territory of Australia.

The present invention relates to isolated strains of a Streptomyces spp. which are endophytes of dicotyledonous plants. The endophytic Streptomyces spp. of the present invention produce biologically active substances, e.g., the munumbicins and kakadumycins, that have promising biological activities of commercial interest. The Streptomycetes described herein are the first endophytes of the order Actinomyces isolated from higher plants, i.e., dicotyledonous or woody plants including trees, shrubs, and vines. The methods described herein allow the selection of, particularly, endophytic Streptomycetes by isolating strains, and purifying and characterizing the bioactive components of these microorganisms.

The term "endophytes" is defined herein as plant-associated microorganisms that live in the interstitial spaces of living plant tissues (Bacon and White, 2000). Higher plants may host one or more endophytic microbes, which include fungi, bacteria, and actinomycetes. Endophytes reside in the tissues beneath the epidermal cell layers. It is well understood that endophytic infections are inconspicuous (Bacon and White, 2000). As a result, the host tissues are transiently symptomless and colonization of the tissues is internal to the surface of the plant. The exact physical relationship of the endophyte to the plant remains obscure, because it is extremely difficult, for example, by electron microscopic techniques, to find an endophyte within plant issues. The relationship that any given endophyte establishes with the plant likely varies from truly symbiotic to something bordering on pathogenic.

While the Actinomycetes, as a group, are the world's greatest biological source of antibiotics with over 2000 that have been reported (Waksman, 1967; Arai, 1976), none have ever been isolated that are endophytic on higher plants. The single microbial genus that has contributed the greatest wealth of antibiotic substances to the world is Streptomyces spp. (Waksman, 1967). The successful isolation of representatives of this important group of microorganisms, as endophytes of higher plants, provides an entirely new source of biologically active products.

In the present invention, the isolation of specific endophytic Streptomycetes that produce antibiotics or other biologically active compounds of interest involves selecting one or more plants as a source of the endophyte. Usually this selection process is conducted on the basis of the environment, age, or natural history of a given plant. Such selection methods involve culturing tissue from the interior region of a dicotyledonous plant, e.g., trees, vines, and shrubs, on nutrient media for a time sufficient to permit colony formation by a strain of endophytic Streptomyces spp. associated with the plant tissue and selecting one or more Streptomyces sp. strains demonstrating the biological activity of interest. Various means can be used to select the endophytic Streptomyces spp. strains, and the strains can be tested through any of numerous methods known in the art to discover a biological activity of interest, either by measuring some activity of the strains directly, i.e., by zones of inhibition, or by preparing and testing extracts or purified compounds from the strains. The biological activity of interest can control or inhibit growth or proliferation of cells, such as cancer cells, or can possess an antibiotic property against a pathogenic organism, such as fungal pathogens, viral pathogens, bacterial pathogens, insect pathogens, or parasitic organisms.

In a preferred embodiment, the endophytic streptomycete is Streptomyces munumbi. Streptomyces munumbi was isolated from Kennedia nigriscans, as described herein. Kennedia nigriscans (snakevine) was obtained from the Northern Territory of Australia where various Aboriginal groups use the ground up mass of snakevine to promote the healing of skin wounds and infections. The snakevine is also known as "mangerrporlo" in Dalabon and Mayali. Streptomyces munumbi are capable of producing a set of novel compounds, designated the munumbicins, each of which contributes distinctive reddish-orange coloration to cultures.

Streptomyces munumbi was speciated as follows. The earlier dichotomous taxonomic key of Waksman and Henrici separates the Streptomyes spp. on the basis of their parasitic or saprophytic relationships with other organisms (Waksman and Lechevalier 1953). Thus, because of its unique endophytic relationship to one host plant—namely Kennedia nigriscans, this Streptomycete does not fit into this scheme for classification. By definition, while living in its plant host, an endophyte does not produce or cause any symptoms on its host, thus making it neither a parasite nor a saprophyte. Also, because of this host-microbe relationship, this microorganism also does not mesh with the classification scheme of Krassilnikov (Waksman and Lechevalier 1953). More recently, individuals working with novel antibiotic-producing isolates of Streptomyces sp. have somewhat arbitrarily assigned species names to this group of organisms on the basis of the bioactive molecule(s) made by them (Goodfellow et al., 1988; Arai, 1976). All earlier classification schemes seem to take into account the ability of an isolate to produce pigmentation in culture.

Figure 2:
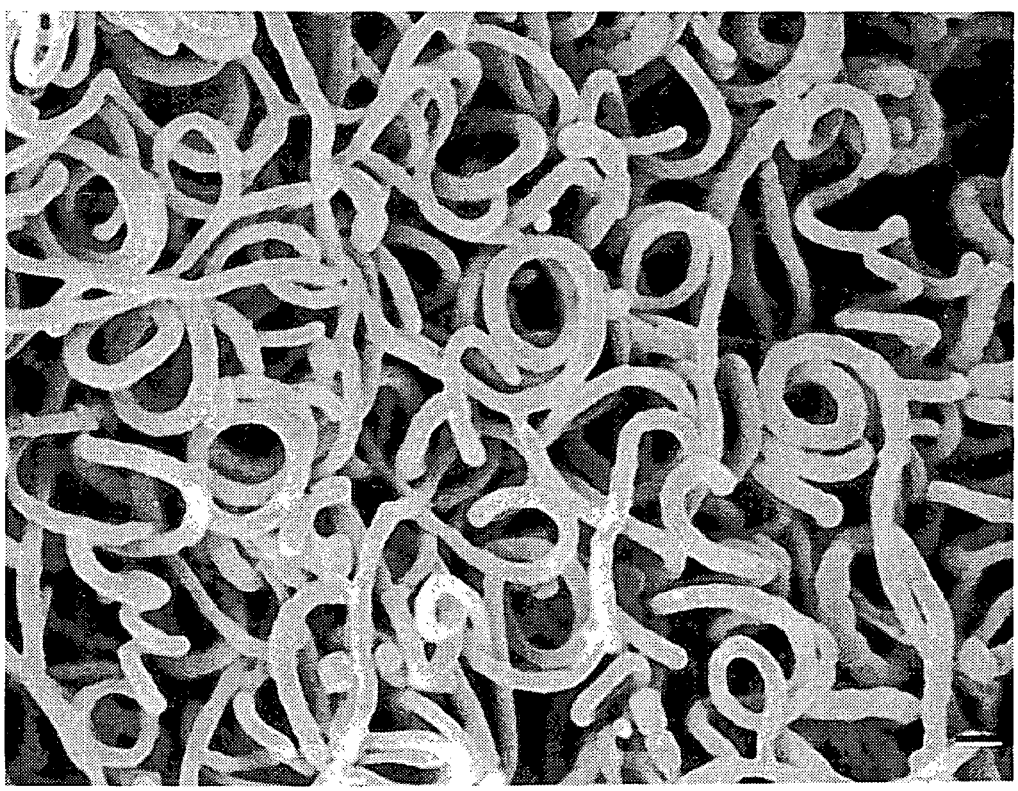
FIG. 2 shows a scanning electron micrograph of *Streptomyces munumbi* grown on gamma-irradiated carnation leaves. The bar equals 1 micron.
Figure 3:
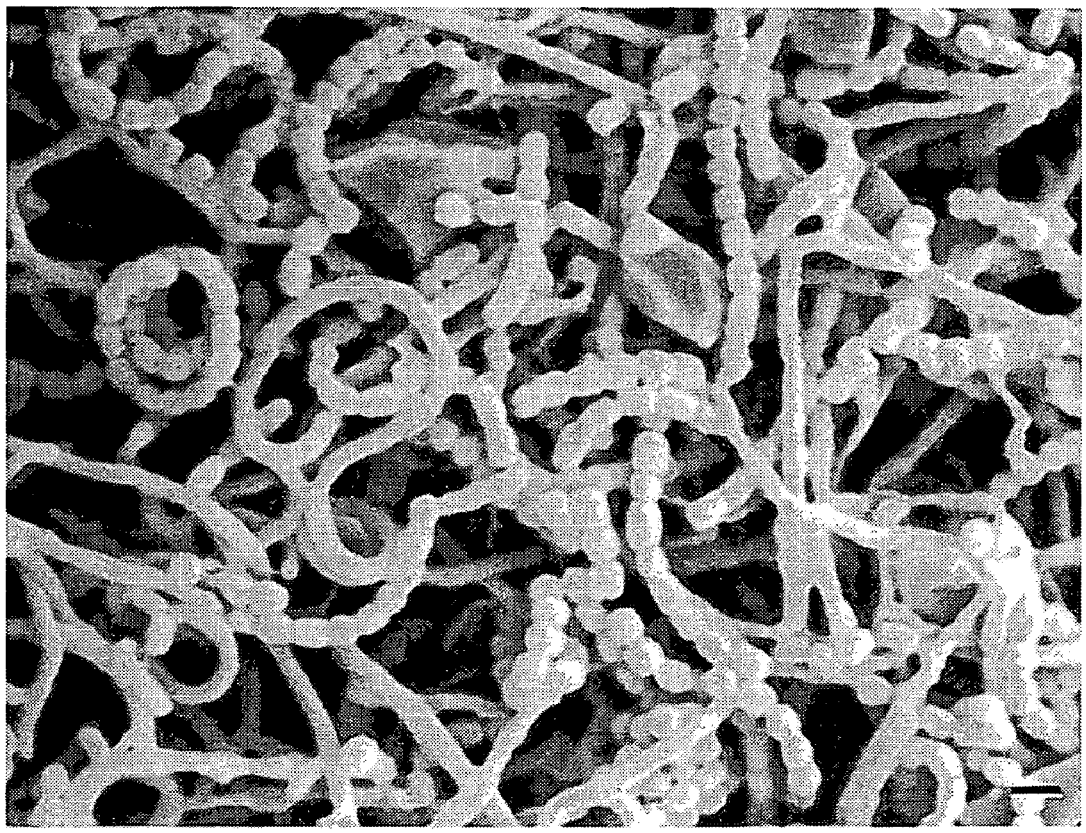
FIG. 3 shows a scanning electron micrograph of *Streptomyces munumbi* grown on steam sterilized pieces of snakevine (*Kennedia nigriscans*). The bar equals 1 micron.

Streptomyces munumbi may have a host specific relationship with Kennedia nigriscans, as it is host selective and symbiotic, since there is some dependency on the host plant to supply substances needed for spore formation. The antibiotic substances of the Streptomycete likely protect the plant (FIGS. 2 and 3). For these reasons, this unique endophytic Streptomycete has been given a tentative species designation which is the proposed binomial-Streptomyes munumbi Strobel, Hess, and Castillo. This organism was deposited as Streptomyces munumbi culture no. 2101 with the Montana State University culture collection. Culture no. 2101 has also been deposited with the Agricultural Research Service Patent Culture Collection, Northern Regional Research Center, 1815 University Street, Peoria, Ill., 61604, as NRRL 30562, with a deposit date of Mar. 7, 2002.

The methods used in the present invention to isolate Streptomyces munumbi NRRL 30562 are applicable to the discovery of numerous other slow growing streptomycetes found in higher plants. The successful isolation of representatives of this important group of microorganisms, as endophytes of higher plants, thus provides a new source of biologically active products. Strains of streptomycetes as sources for biological activity can be obtained from a diverse array of dicotyledonous plants including, in addition to *Kennedia nigriscans*, but not limited to, *Ceiba pentandra*, *Chiliotrichum diffusum*, *Desfontainia spinosa*, *Drymis winteri*, *Dunalia purpurea*, *Grevellia pteridifolia*, *Misodendrum punctulatum*, *Monstera speciosa*, *Nothofagus antartica*, *Nothofagus betuloides*, *Nothofagus pumilio*, *Podocarpus nubigena*, *Taxus wallichiana*, and *Theobroma cacao*.

In another preferred embodiment, the endophytic streptomycete is *Streptomyces* sp. A35-1, which was isolated from a plant known as fern-leafed Grevellia (*Grevellia pteridifolia*). Fern-leafed Grevellia grows in moist river bottoms of the Northern Territory of Australia. *Streptomyces* sp. A35-1 produces a set of novel compounds, designated the kakadumycins.

*Streptomyces* sp. A35-1, in all respects, fits the scheme and descriptions of being a streptomycete (Waksman and Lechevalier 1953; Goodfellow et al., 1988; Arai, 1976). This organism was deposited as *Streptomyces* sp. culture number A35-1 with the Montana State University culture collection. *Streptomyces* sp. A35-1 has also been deposited with the Agricultural Research Service Patent Culture Collection, as NRRL 30566, with a deposit date of Mar. 7, 2002.

In a further embodiment of the present invention, other biologically active endophytic Streptomycetes isolated according to the methods described herein were deposited with the Agricultural Research Service Patent Culture Collection, as NRRL 30563, NRRL 30564, NRRL 30565, and NRRL 30567, each with a deposit date of Mar. 12, 2002.

Munumbicins and Kakadumycins

The present invention also relates to biologically active agents useful in treating or preventing various conditions. The biologically active agents can be the *Streptomyces* strains themselves, crude extracts obtained by cultivating such strains under culture conditions, or compounds isolated from the strains. In this manner the invention also provides novel biologically active extracts and compounds.

The biologically active agents of the present invention can be used to control a range of pathogenic organisms, diseases, or conditions. The agent is provided in an amount effective to inhibit the pathogenic organism or condition for a time and under conditions permitting the agent to inhibit the pathogenic organism or condition.

In a preferred embodiment, the biologically active agents can be used to control parasitic organisms, including, but not limited to, infections caused by Gram positive bacteria and also some Gram negative bacteria. In a more preferred embodiment, the compounds are useful in the control of a parasitic *Plasmodium* spp., for example, *Plasmodium falciparum* and *Plasmodium vivax*.

In another preferred embodiment, the biologically active agents can be used to control bacterial pathogens. Pathogenic bacterial organisms which may be controlled by the biological agents include, but are not limited to, strains of *Escherichia coli*, *Shigella dysenteriae*, *Klebsiella pneumoniae*, *Pseudomonas aeruginosa*, *Pseudomonas syringae*, *Burkholderia cepacia*, *Acinetobacter boumanii*, *Neisseria gonorrhoeae*, *Haemophilus influenzae*, *Stenotrophomas maltophilia*, *Staphylococcus* spp., *Staphylococcus aureus*, *Staphylococcus aureus* MRSA, *Staphylococcus aureus* GISA, *Streptococcus pneumoniae*, *Enterococcus* spp., *Enterococcus faecalis*, *Enterococcus faecalis* VRE, *Enterococcus faecium*, *Mycobacterium* spp., *Mycobacterium tuberculosis*, *Bacillus anthracis*, *Erwinia carotovora*, *Vibrio fischeri*, *Streptococcus* spp., and *Acinetobacter* spp.

In another preferred embodiment, the biologically active agents can be used to control diverse fungal pathogens including, but not limited to, *Pythium ultimum*, *Rhizoctonia solani*, *Aspergillus* spp., *Aspergillus fumigatus*, *Fusarium oxysporum*, *Botrytis alli*, *Alternaria helianthi*, *Phytophthora infestans*, *Penicillum* sp., *Sclerotinia sclerotiorum*, *Cryptococcus neoformans*, *Histoplama capsulatum*, *Blastomyces dermatitidis*, *Cochliobolus carbonum*, *Geotrichum candidum*, *Phytophthora cinnamomi*, *Rhizoctonia solani*, *Candida tropicalis*, *Candida globrata*, and *Candida albicans*, *Candida tropicalis*, and *Candida parapsilosis*.

In another preferred embodiment, the biologically active agents can be used to protect against viral pathogens, or against an array of invertebrate pathogens.

In another preferred embodiment, the endophytic streptomycetes strains produce compounds having biological activity against cancer cells, and can be used in the treatment of cancer. Such cancer cells include, but are not limited to, human lung cancer epithelial A549 cells, human cervical cancer epithelial ME180 cells, and human breast cancer epithelial BT-20 cells.

Munumbicins

The Streptomycete designated *Streptomyces munumbi* NRRL 30562 produces a series of chemically unique compounds that are peptide antibiotics, which have been designated the "munumbicins." To isolate the munumbicins, *Streptomyces munumbi* may be fermented and the broth extracted with an organic solvent, e.g., methylene chloride, and the contents of the residue purified by bioassay guided high performance liquid chromatography using the fungus *Pythium ultimum* as the test organism. The munumbicin preparation primarily contains 4 functionalized peptides designated Munumbicins A, B, C, and D. Munumbicins A, B, C, and D have masses of 1326.5, 1269.6, 1298.5, and 1312.5, respectively, by mass spectroscopy.

Amino acid analysis of the munumbicins reveals that the munumbicins as a class of biologically active compounds comprise a peptide chain having Glx (glutamic acid or glutamine), proline (Pro), threonine (Thr), and valine (Val). Each of the four compounds produce chromatographic profiles consistent with the presence of Glx, Pro, Thr, and Val.

In a preferred embodiment, the munumbicin is munumbicin A having UV absorbances at 218 and 240 nm; HPLC retention time of 69.9 minutes on a Microsorb 100-5 C-18 column, 250×4.6 mm, using 20% acetonitrile:80% water for 90 minutes as an initial elution solvent programmed to a final concentration of 80% acetonitrile; and a mass of 1326.5 daltons.

In another preferred embodiment, the munumbicin is munumbicin B having UV absorbances at 208, 240, 420 and 440 nm; a retention time of 68.5 minutes on a Microsorb 100-5 C-18 column, 250×4.6 mm, using 20% acetonitrile: 80% water for 90 minutes as an initial elution solvent programmed to a final concentration of 80% acetonitrile; and mass of 1269.6 daltons.

In another preferred embodiment, the munumbicin is munumbicin C having UV absorbances at 220, 240, 416, and 440 nm; a retention time of 67.8 minutes on a Microsorb 100-5 C-18 column, 250×4.6 mm, using 20% acetonitrile: 80% water for 90 minutes as an initial elution solvent programmed to a final concentration of 80% acetonitrile; and a mass of 1298.5 daltons.

In another preferred embodiment, the munumbicin is munumbicin D having UV absorbances at 221, 314, 404 nm; a retention time of 45 minutes on a Microsorb 100-5 C-18 column, 250×4.6 mm, using 20% acetonitrile:80% water for 90 minutes as an initial elution solvent programmed to a final concentration of 80% acetonitrile at a flow rate of 2 ml/minute; and a mass of 1312.5 daltons.

The general nature of the $^1$H NMR spectrum of each of the munumbicins suggests that the chemical nature of these compounds is that of a highly functionalized peptide. In a preferred embodiment, the $^1$H NMR spectrum (CDCl$_3$, 500 MHz) of a munumbicin B comprises $^1$H chemical shifts shown in FIG. 5.

Figure 7:
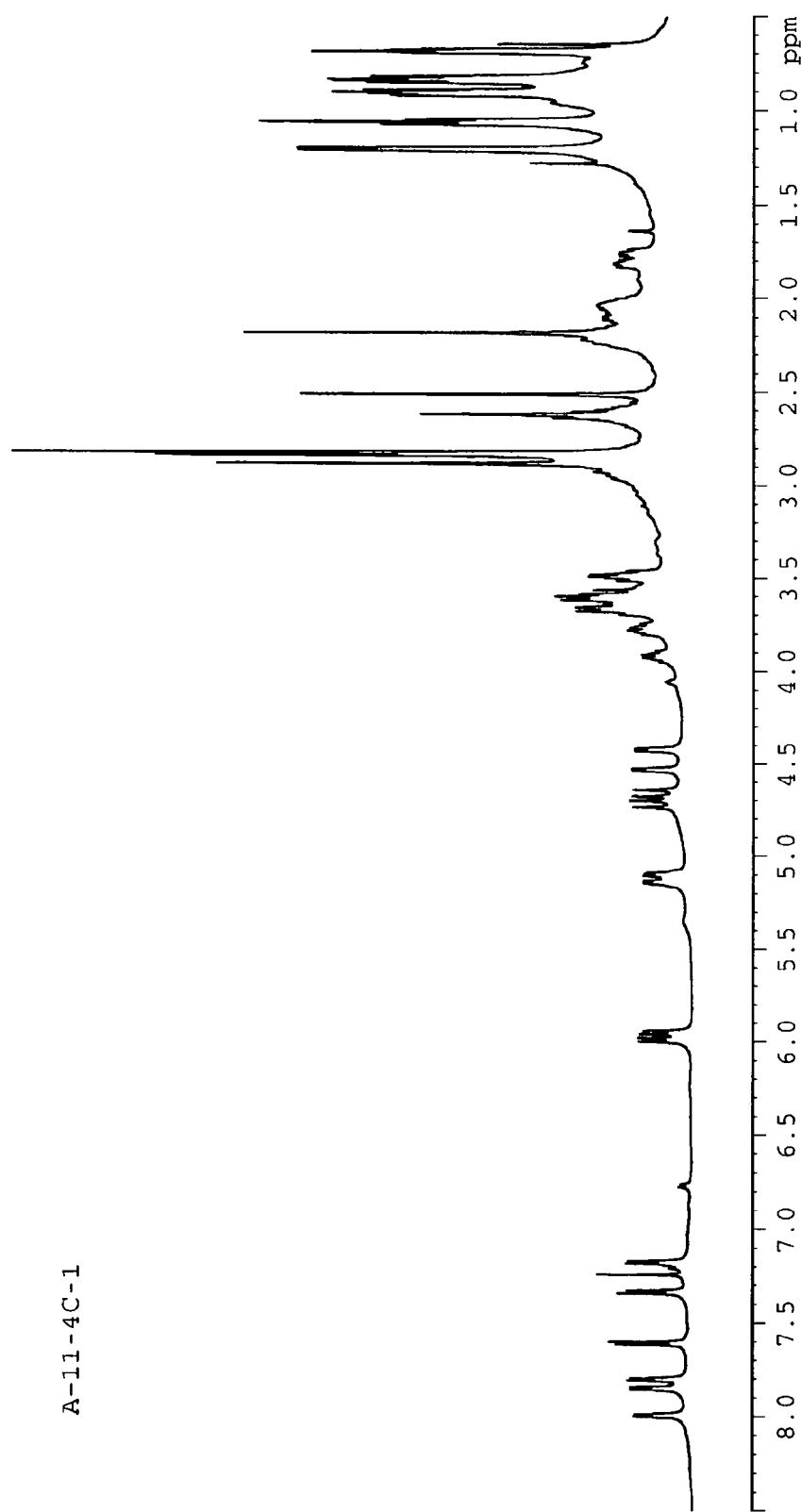
FIG. 7 shows the $^1$H NMR spectrum of munumbicin C (CDCl$_3$, 500 MHz).

In another preferred embodiment, the $^1$H NMR spectrum (CDCl$_3$, 500 MHz) of a munumbicin C comprises $^1$H chemical shifts shown in FIG. 7.

Figure 9:
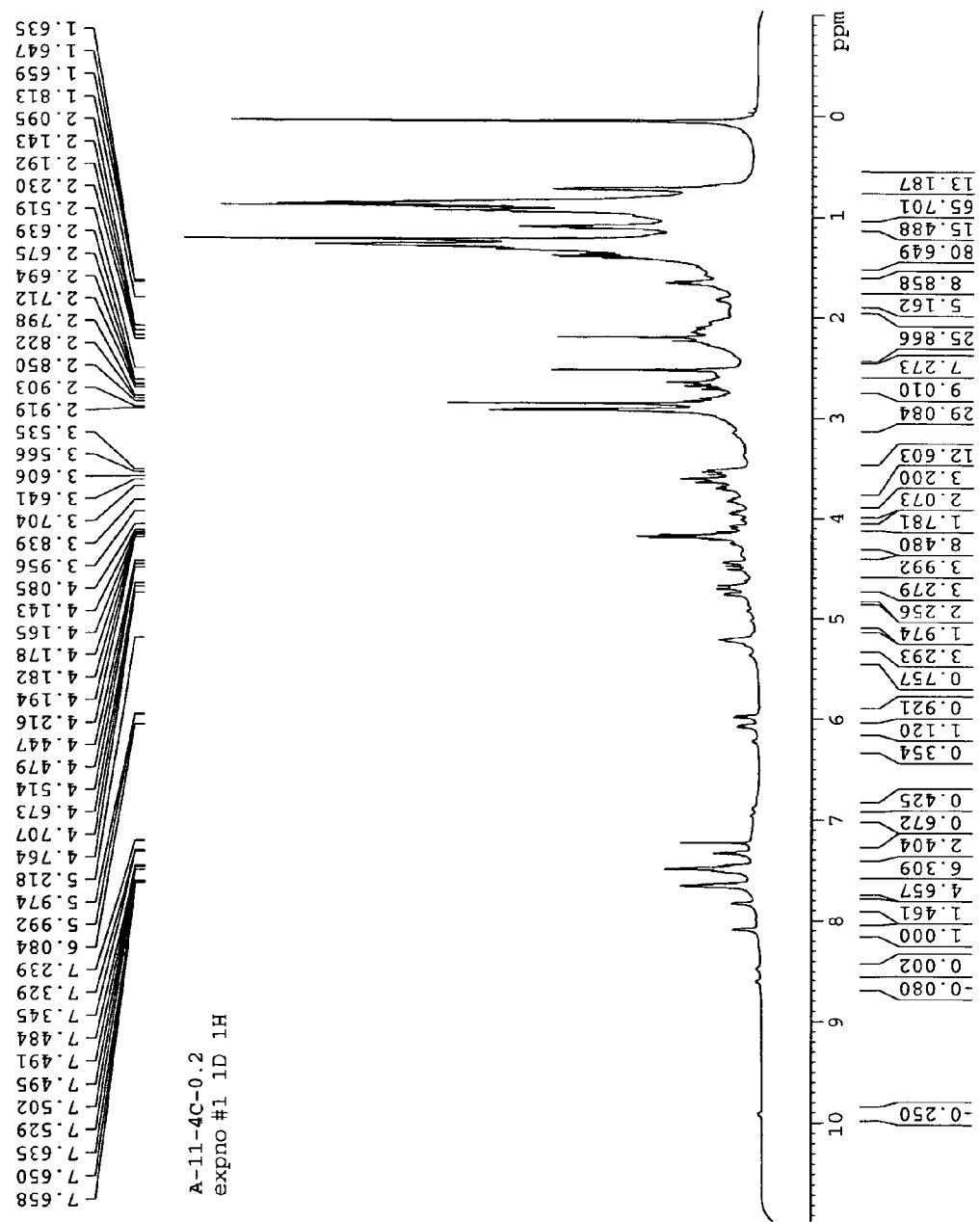
FIG. 9 shows the $^1$H NMR spectrum of munumbicin D (CDCl$_3$, 500 MHz).

In another preferred embodiment, the $^1$H NMR spectrum (CDCl$_3$, 500 MHz) of a munumbicin D comprises $^1$H chemical shifts shown in FIG. 9.

Figure 6:
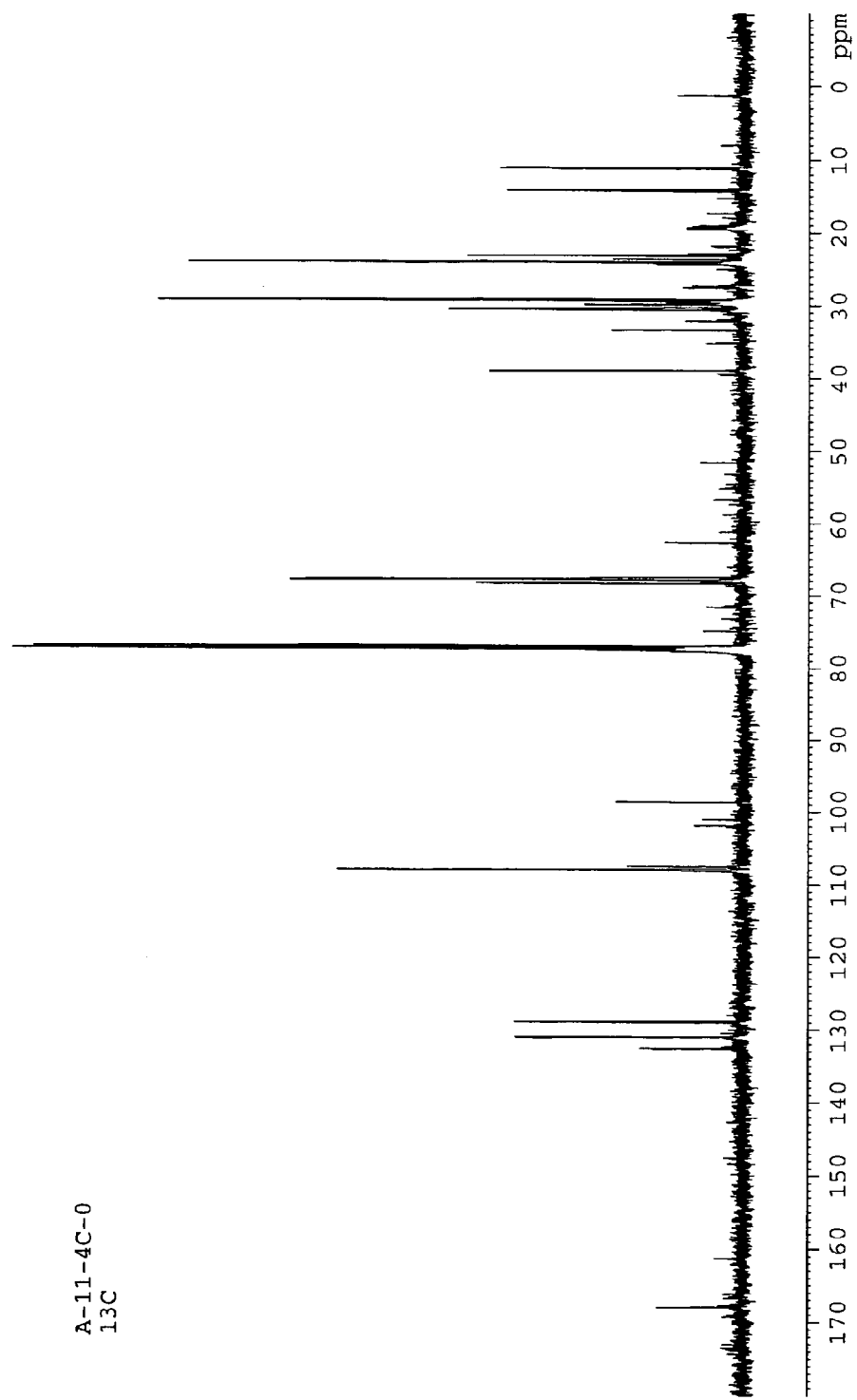
FIG. 6 shows the $^{13}$C NMR spectrum of munumbicin B (CDCl$_3$, 500 MHz).

In another preferred embodiment, the $^{13}$C NMR spectrum for purified munumbicin B comprises $^{13}$C chemical shifts shown in FIG. 6.

Figure 8:
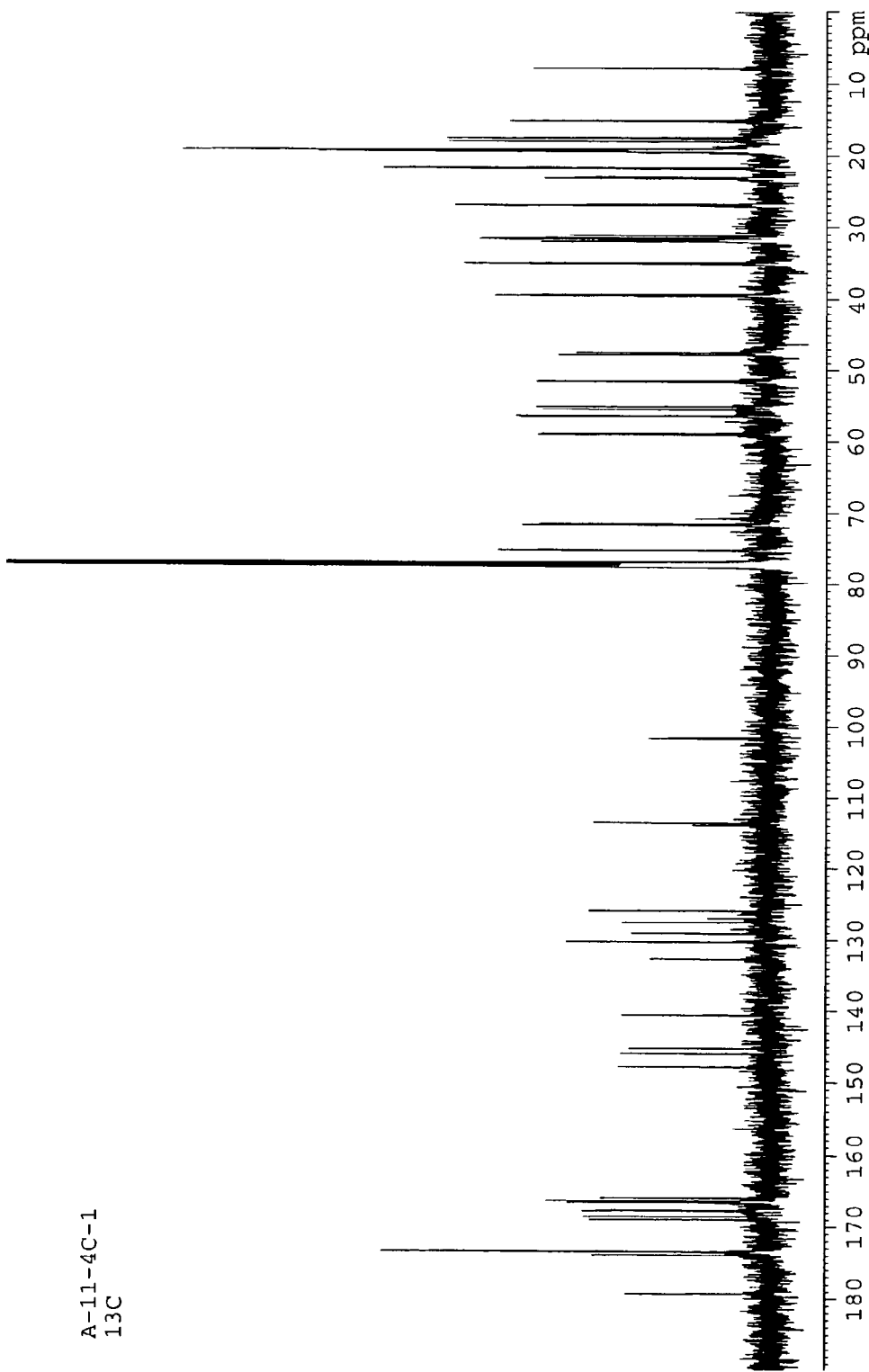
FIG. 8 shows the $^{13}$C NMR spectrum of munumbicin C (CDCl$_3$, 500 MHz).

In another preferred embodiment, the $^{13}$C NMR spectrum for purified munumbicin C comprises $^{13}$C chemical shifts shown in FIG. 8.

Figure 10:
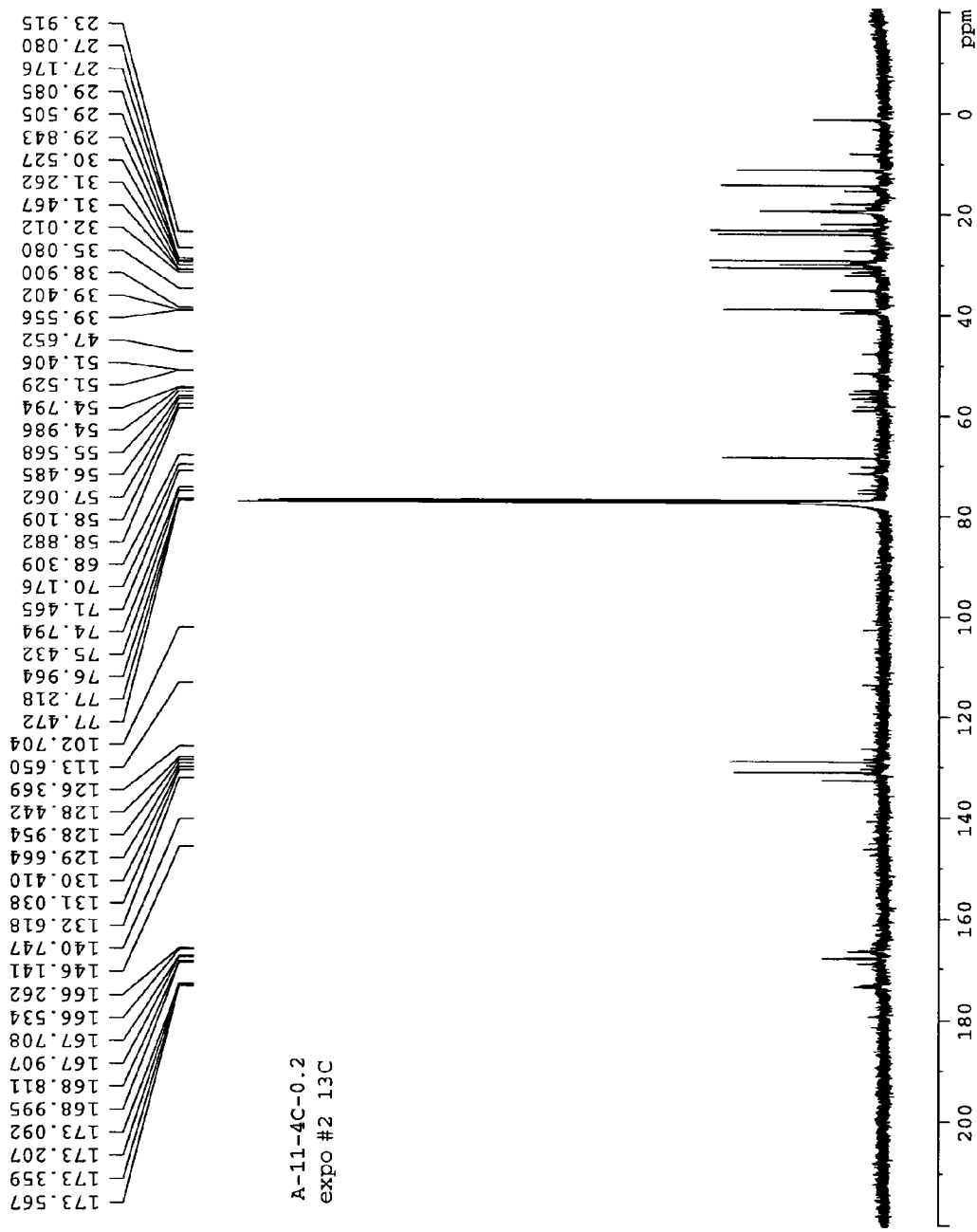
FIG. 10 shows the $^{13}$C NMR spectrum of munumbicin D (CDCl$_3$, 500 MHz).

In another preferred embodiment, the $^{13}$C NMR spectrum for purified munumbicin D comprises $^{13}$C chemical shifts shown in FIG. 10.

Numerous other related compounds, or minor munumbicins, possessing bioactivity, with differing masses and lower quantities were also present in the culture broth extract of *Streptomyces munumbi*. With few exceptions, the peptide portion of each component contained only the common amino acids threonine, aspartic acid (asparagine), glutamic acid (glutamine), valine, and proline, in varying ratios. Minor component munumbicins include those having a mass of 1266 daltons, 1314.5 daltons, 1328.5 daltons, and 1346 daltons, respectively, by mass spectroscopy.

The munumbicins possess widely differing biological activities depending upon the target organism. For instance, munumbicin B has an MIC of 2.5 micrograms/ml against a methicillin-resistant strain of *Staphylococcus aureus*, whereas munumbicin A is not active against this organism. The MIC (minimum inhibitory concentration) was defined as that concentration of a compound resulting in no visible growth of the test organism.

In general, all munumbicins demonstrate activity against Gram positive bacteria such as *Bacillus anthracis*, and many fungi pathogenic to plants and humans, and multi drug-resistant *Mycobacterium tuberculosis*. Munumbicin A shows activity against gram positive organisms including vancomycin resistant *Enterococcus faecalis* (VRE). Munumbicin B shows activity against *Mycobacterium tuberculosis* with IC$_{50}$s of 10 and 46 micrograms/ml against the drug resistant *Mycobacterium tuberculosis* MDR-P and wild-type strains, respectively. Munumbicin C shows activity against the malaria parasite *Plasmodium falciparum* with an IC$_{50}$ of 6.5 nanograms/ml compared to an IC$_{50}$ of chloroquine of 7 nanograms/ml. Munumbicin D shows strong activity against the malarial parasite *Plasmodium falciparum*, having an IC$_{50}$ Of 4.5±0.07 nanograms/ml.

All the munumbicins are active against *Pythium ultimum* and plant pathogens including *Rhizoctonia solani, Phytophthora cinnamomi, Sclerotinia sclerotiorum*, and *Pseudomonas syringae*. All the munumbicins are active against gram positive bacteria including *Staphylococcus* species, *Streptococcus pneumoniae, Enterococcus* species, *Bacillus subtilis*, and *Listeria monocytogenes*. They are also active against drug resistant strains such as vancomycin resistant *Enterococcus faecalis* (VRE), methicillin resistant *Staphyloccus aureus* (MRSA), glycopeptide intermediate and *Staphylococcus aureus* (GISA). All munumbicins are also cytotoxic to cancer cell lines.

The munumbicins can, therefore, be used to treat or protect plants challenged or infected by an entire series of plant pathogens, and may be used to treat diseases in the field, soil or in post harvest applications. Similarly, the munumbicins are useful as agents to treat certain pathogenic conditions, from cancer to infections by bacterial, fungal, viral and parasitic pathogens of animals. Munumbicins have relevance to human medicine and drug discovery as the munumbicins show activity against a range of important diseases including tuberculosis, malaria, and certain diseases caused by Gram positive bacteria.

Kakadumycins

The Streptomycete designated *Streptomyces* sp. A35-1 (NRRL 30566) produces a series of chemically unique compounds that are peptide antibiotics, which have been designated the "kakadumycins." To isolate the kakadumycins, *Streptomyces* sp. A35-1 may be fermented and the broth extracted with an organic solvent, e.g., methylene chloride, and the contents of the residue purified by bioassay guided high performance liquid chromatography using the fungus *Pythium ultimum* as the test organism. The kakadumycin preparation primarily contains at least three bioactive peptides designated kakadumycin A, kakadumycin B, and kakadumycin C with masses of 1100.41, 1052.3, and 1068.4, respectively, by mass spectroscopy.

Amino acid analysis of kakadumycin A, reveals that the kakadumycins as a class of biologically active compounds comprise a peptide chain. Amino acid analytical profiles of kakadumycin A show chromatographic profiles consistent with the presence of serine (Ser), alanine (Ala), and an unknown amino acid in a molar ratio of 1:2:3 (3 is estimated). The unknown amino acid is one that has a retention time and chromatographic profile similar to that for proline. However, co-chromatography with proline indicates that the unknown amino acid was distinct from proline. The unknown amino acid found in kakadumycin A is not present in kakadumycin B.

In a preferred embodiment, the kakadumycin is kakadumycin A having UV absorbances at 205, 238, and 315 nm; a retention time of 73 minutes on a Symmetry C-18 column, 150×4.6 mm (3.5 micron), using 20% acetonitrile:80% water for 90 minutes as an initial elution solvent programmed to a final concentration of 80% acetonitrile at a flow rate of 2 ml/minute; and a mass of 1100.41 daltons.

In another preferred embodiment, the kakadumycin is kakadumycin B having UV absorbances at 239, 316, and 272 nm; a retention time of 77.5 minutes on a Symmetry C-18 column, 150×4.6 mm (3.5 micron), using 20% acetonitrile:80% water for 90 minutes as an initial elution solvent programmed to a final concentration of 80% acetonitrile at a flow rate of 2 ml/minute; and mass of 11053.3 daltons.

In another preferred embodiment, the kakadumycin is kakadumycin C having UV absorbances at 204, 221, 246, and 307 nm; a retention time of 107 minutes on a Symmetry C-18 column, 150×4.6 mm (3.5 micron), using 20% acetonitrile:80% water for 90 minutes as an initial elution solvent programmed to a final concentration of 80% acetonitrile at a flow rate of 2 ml/minute; and a mass of 1068.4 daltons.

The general nature of the $^1$H NMR spectra of the kakadumycins suggests that the chemical nature of the compounds is that of a highly functionalized peptide (Silverstein et al., 1991; Strobel et al., 1999). In a preferred embodiment, the $^1$H NMR spectrum (CDCl$_3$, 500 MHz) of a kakadumycin A comprises $^1$H chemical shifts shown in FIG. 12.

Figure 15:
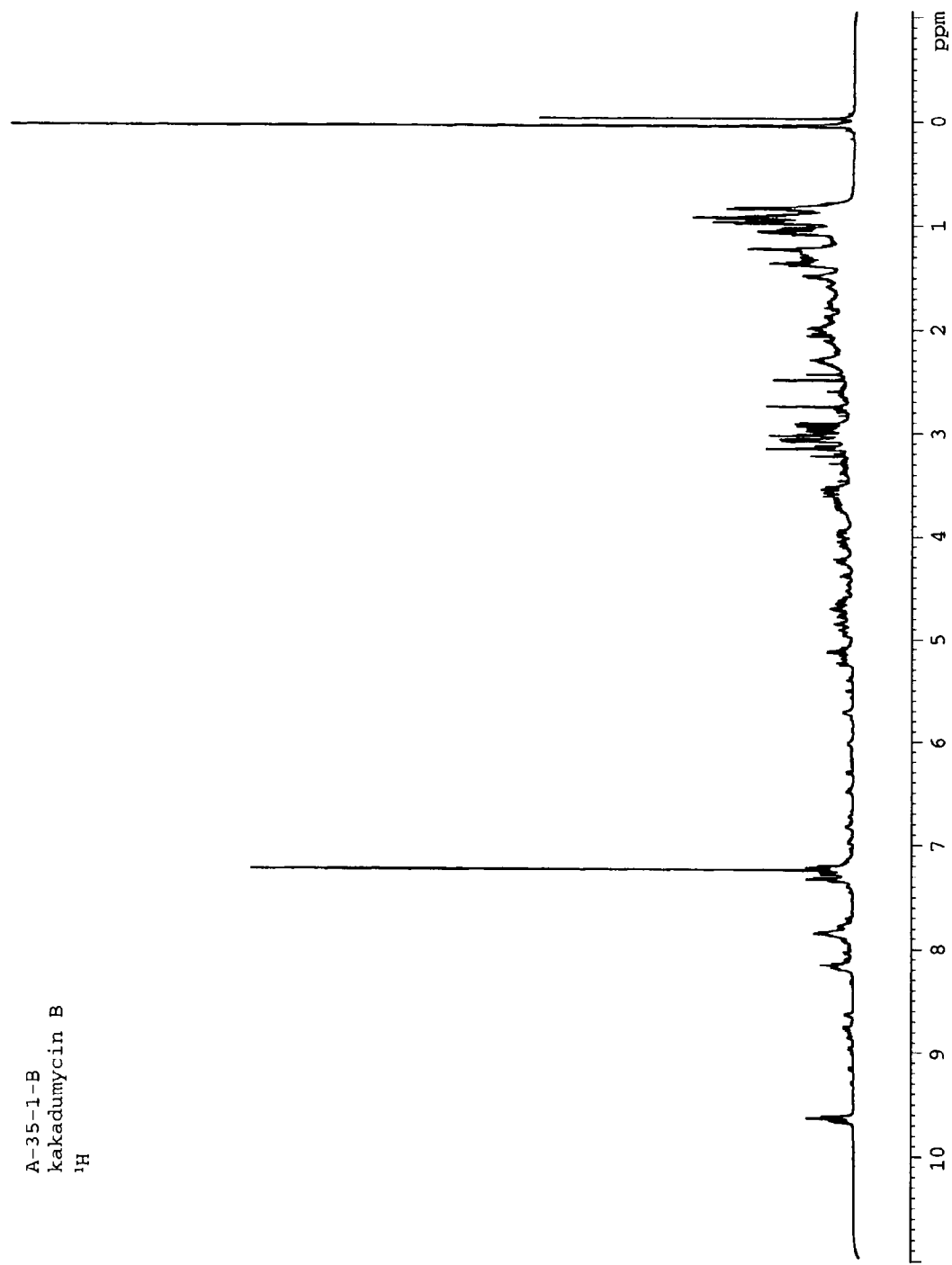
FIG. 15 shows the $^1$H NMR spectrum of kakadumycin B (CDCl$_3$, 500 MHz).

In another preferred embodiment, the $^1$H NMR spectrum (CDCl$_3$, 500 MHz) of a kakadumycin B comprises $^1$H chemical shifts shown in FIG. 15.

Figure 13:
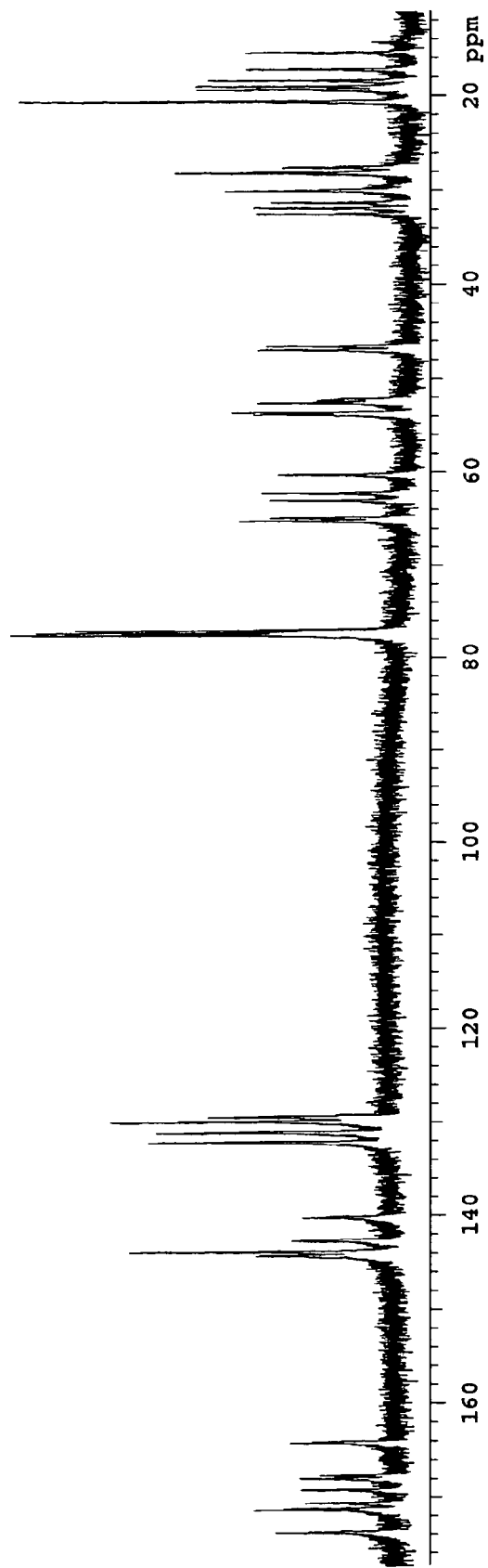
FIG. 13 shows the $^{13}$C NMR spectrum of kakadumycin A (CDCl$_3$, 500 MHz).
Figure 14:
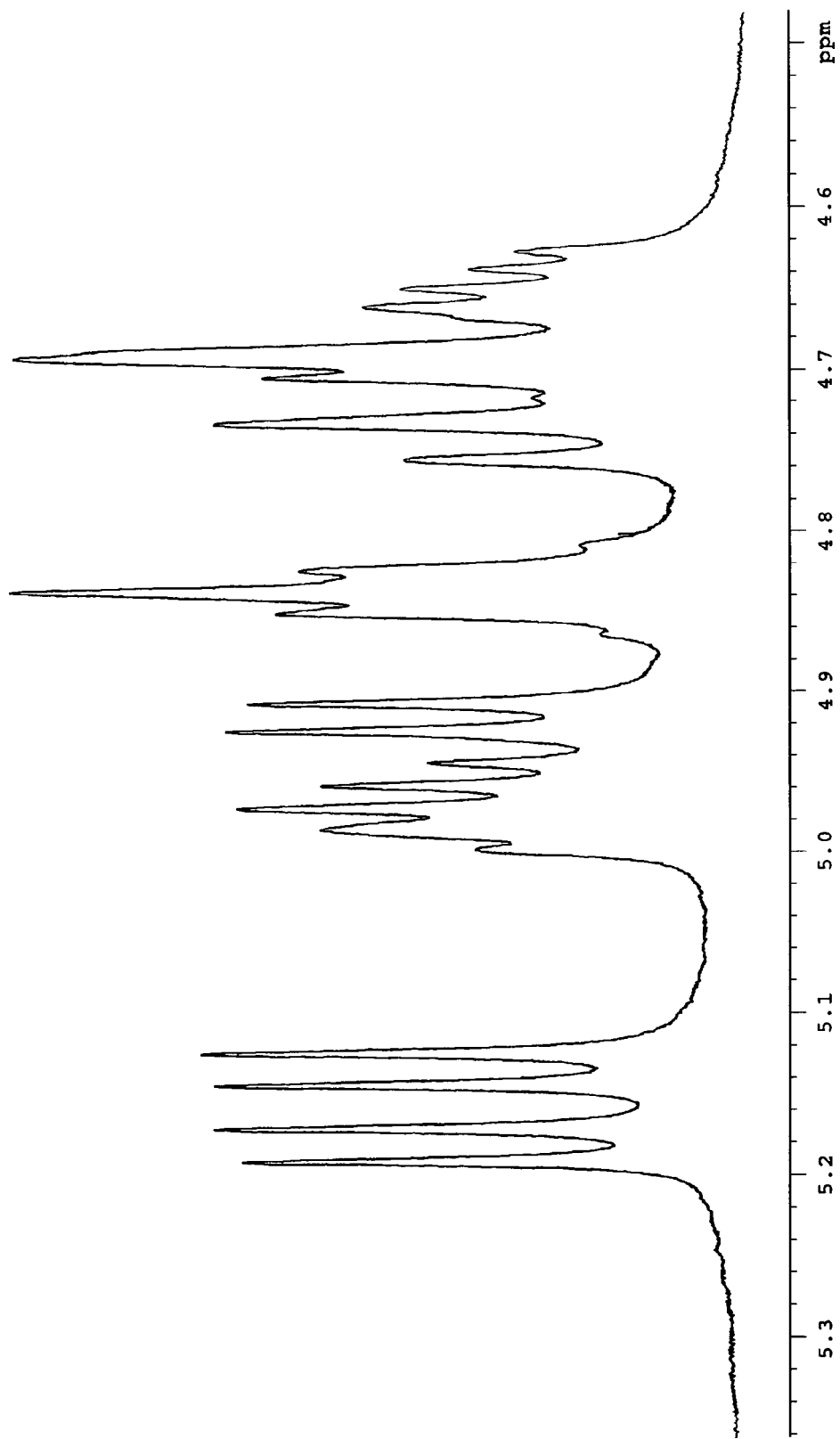
FIG. 14 shows an expanded version of the $^{13}$C spectrum of kakadumycin A showing the region from 4.6-5.3 ppm (CDCl$_3$, 500 MHz).

In another preferred embodiment, the $^{13}$C NMR spectrum for purified kakadumycin A comprises $^{13}$C chemical shifts shown in FIGS. 13 and 14.

In another preferred embodiment, the $^{13}$C NMR spectrum for purified kakadumycin B comprises $^{13}$C chemical shifts shown in FIG. 16.

The kakadumycins can be used to treat or protect plants challenged or infected by an entire series of plant pathogens, and may be used to treat diseases in the field, soil or in post harvest applications. Similarly, the kakadumycins are useful as agents to treat certain pathogenic conditions, from cancer to infections by bacterial, fungal, viral and parasitic pathogens of animals.

The kakadumycins are active against *Pythium* sp., *Phytophthora* sp., *Rhizoctonia* sp., and *Fusarium* sp. fungal species that cause root and stem rots of plants. The kakadumycins are also effective against a number of stem and flower infecting fungi including *Botrytis* sp., *Alternaria* sp., and *Helminthosporium* sp. The kakadumycins are active against *Pythium ultimum* while the munumbicins (A, B, C and D) are much more active than the kakadumycins against plant pathogens including *Rhizoctonia solani, Phytophthora cinnamomi, Sclerotinia sclerotiorum* and *Pseudomonas syringae.*

The kakadumycins are active against gram positive bacteria including *Staphylococcus* species, *Streptococcus pneumoniae, Enterococcus* species, *Bacillus subtilis,* and *Listeria monocytogenes.* They are also active against drug resistant strains such as vancomycin resistant *Enterococcus faecalis* (VRE), methicillin resistant *Staphylococcus aureus* (MRSA), glycopeptide intermediate and *Staphylococcus aureus* (GISA).

The kakadumycins are also cytotoxic to cancer cell lines.

Kakadumycin A has activity against the malaria parasite *Plasmodium falciparum* with an IC$_{50}$ of 4.5 nanograms/ml compared to an IC50 of chloroquine of 7 nanograms/ml. Kakadumycin A also has activity against *Bacillus anthracis* strains with an MIC of 0.3 to 0.55 micrograms/ml.

Methods of Production

The present invention also relates to methods for producing a biological agent of the invention. The biological agent may be an endophytic Streptomycete; an extract of the endophytic Streptomycete, or a compound obtained from the endophytic Streptomycete, e.g., munumbicin or kakadumycin, having the biological activity of interest. The methods comprise cultivating a strain of an endophytic *Streptomyces* spp. and recovering the biological agent from the culture medium. If the biological agent is a munumbicin or kakadumycin, it may be desirable thereafter to form the free acid or a salt or ester by methods known per se.

The endophytic *Streptomyces* sp., or a high yielding or otherwise modified mutant thereof, may be used in the methods of the present invention to produce the biologically active agents.

The endophytic *Streptomyces* spp. are cultivated in a nutrient medium suitable for production of the heterologous biological substance using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

When used herein, the term "cultivation" means the growth of an endophytic *Streptomyces* spp. in the presence of assimilable sources of carbon, nitrogen and mineral salts. Such aerobic growth may take place in a solid or semi-solid nutritive medium, or in a liquid medium in which the nutrients are dissolved or suspended. The cultivation may take place on a surface or by submerged culture. The nutritive medium may be composed of complex nutrients or may be chemically defined.

The nutrient media which may be used for the cultivation of the endophytic *Streptomyces* spp. may contain, in the range 0.1-10%, a complex organic nitrogen source such as yeast extract, corn steep liquor, vegetable protein, seed protein, hydrolysates of such proteins, milk protein hydrolysates, fish and meat extracts, and hydrolysates such as peptones. Alternatively, chemically defined sources of nitrogen may be used such as urea, amides, single or mixtures of common amino acids such as valine, asparagine, glutamic acid, proline, and phenylalanine. Carbohydrate (0.1-5%) may be included in the nutrient media and starch or starch hydrolysates such as dextrin, sucrose, lactose or other sugars or glycerol or glycerol esters may also be used. The source of carbon may also be derived from vegetable oils or animal fats. Carboxylic acids and their salts can be included as a source of carbon for growth and production of beta-lactamase inhibitors. A particularly suitable low cost medium is one containing soya bean flour plus dried malt distillers solubles plus dextrin.

Mineral salts such NaCl, KCl, MgCl$_2$, ZnCl$_2$, FeCl$_3$, Na$_2$SO$_4$, FeSO$_4$, MgSO$_4$ and Na$^+$ or K$^+$ salts of phosphoric acid may be added to the media described above particularly if chemically defined. CaCO$_3$ may be added as a source of Ca$^{++}$ ions or for its buffering action. Salts of trace elements such as nickel, cobalt or manganese may also be included. Vitamins may be added if desired.

The present invention is also directed to a mutant of an endophytic *Streptomyces* wherein the amount of the munumbicin or kakadumycin produced by the mutant is greater than the amount of the substance produced by a corresponding parental strain. The present invention is further directed to methods for obtaining such a mutant. A "parental strain" as defined herein is the original endophytic *Streptomyces* strain before mutagenesis which leads to the mutated strain. The term "mutant" includes any mutant strain which arises spontaneously or through the effect of an external agent whether that agent is applied deliberately or otherwise.

In one embodiment, a munumbicin or kakadumycin of the present invention is obtained from a mutant of an endophytic *Streptomyces* strain, particularly, a *Streptomyces* strain selected from the group consisting of NRRL 30562, NRRL 30566, NRRL 30563, NRRL 30564, NRRL 30565, and NRRL 30567, wherein the substance is produced in an amount greater than the amount of the substance produced by a corresponding parental strain. Suitable methods of producing mutant strains are well-known to those in the art, and include, for example, ionizing radiation (such gamma-rays or X-rays), UV light, UV light plus a photosensitizing agent (such as 8-methoxypsoralen), nitrous acid, hydroxylamine, purine or pyrimidine base analogues (such as 5-bromouracil and N-methyl-N'-nitro-N-nitrosoguanidine), acridines, alkylating agents (such as mustard gas, ethyl-methane sulphonate), hydrogen peroxide, phenols, formaldehyde, and heat. Alternatively, mutants may be produced through genetic techniques such as recombination, shuffling, transformation, transduction, lysogenisation, lysogenic conversion, and selective techniques for spontaneous mutants. Specifically, one method of mutating an endophytic Streptomyces strain and selecting such a mutant comprises the following procedure: (i) the parental strain is treated with a mutagen; (ii) the thus presumptive mutants are grown in a medium suitable for selection of a mutant strain; and (iii) the mutant strain is selected on the basis of increased production of a compound of the present invention.

According to a preferred embodiment of this method, the selected colonies are grown in a normal production medium, and a final selection for such mutants is performed.

The present invention also relates to methods for obtaining a "substantially pure" munumbicin and kakadumycin of the present invention. A "substantially pure" munumbicin or kakadumycin is defined herein as a munumbicin or kakadumycin which contains less than 5% contaminants. Munumbicins and kakadumycins, or other compounds of endophytic Streptomyces spp., may be extracted from the culture filtrate by a variety of methods known to the art. The cells of the Streptomyces spp. are normally first removed from the fermentation by filtration or centrifugation before such extraction procedures are commenced. Precipitation by solvent extraction from culture filtrate, which may use an adjusted to acid pH values and methods based on the anionic nature of the metabolite such as the use of anion exchange resins may be utilized. Other primary methods of isolation which may be used include conventional methods such as adsorption onto carbon, precipitation, salting out, molecular filtration, or any method known in the art.

Compositions and Uses

The present invention also relates to compositions comprising a biological agent of the invention. The biological agent may be an endophytic Streptomycete, an extract of the endophytic Streptomycete, or a compound obtained from the endophytic Streptomycete, e.g., munumbicin or kakadumycin, having the biological activity of interest. The composition can include a suitable carrier, or may comprise the agent affixed to a substrate. The compositions comprising a biologically active agent of the present invention can be used to control a range of pathogenic organisms, diseases, or conditions. The composition may also find use as applied to a substrate. The agent is provided in an amount effective to inhibit the pathogenic organism or condition for a time and under conditions permitting the agent to inhibit the pathogenic organism or condition. Different compositions will be required for administration to plants, humans and animals in unit dosage forms, such containing suitable quantities of the compounds.

Common carriers and excipients include, but are not limited to, corn starch or gelatin, lactose, sucrose, microcrystalline cellulose, kaolin, mannitol, dicalcium phosphate, sodium chloride, and alginic acid.

The munumbicins, kakadumycins, or other compounds, or a salt or ester thereof, obtainable from an endophytic Streptomyces spp. can be formulated into a pharmaceutical composition, which comprises the compound, together with a pharmaceutically acceptable carrier.

The compound may be in the form produced by the endophytic Streptomyces spp., or the result of further chemical modification, for instance to reduce toxicity and perhaps to increase efficacy. This approach has been effectively taken with another antibiotic family, obtained from a plant associated microbe—Pseudomonas syringae, namely, the pseudomycins (Ballio et al., 1994). A specific pseudomycin has been subjected to modifications by organic synthesis and has yielded a derivative that is no longer toxic to mammalian systems and yet remains effective against human pathogenic fungi (Zhang et al., 2001a; Zhang et al., 2001b). Since the munumbicins have numerous functional groups, especially those associated with the peptide portion of the molecule, such chemical derivatization would be an option.

The pharmaceutical compositions of the invention include those in a form adapted for oral, topical, or other potential use, and may be used for the treatment of infection in mammals including humans.

Examples of suitable unit dosage forms in accord with the present invention are tablets, capsules, pills, suppositories, powder packets, wafers, granules, cachets, teaspoonfuls, tablespoonfuls, dropperfuls, ampoules, suspensions, syrups, vials, aerosols with metered discharges, segregated multiples of any of the foregoing, and other forms as herein described. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics. The concentration of a compound in the unit dosage may vary, for example, from about 1 percent to about 50 percent depending on the particular form of the compound and its solubility and the dose desired.

For oral administration, either solid or fluid unit dosage forms can be prepared. For preparing solid compositions such as tablets, the desired compound is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Disintegrators commonly used in the compositions of the invention include croscarmellose, microcrystalline cellulose, corn starch, sodium starch glycolate, and alginic acid. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can also be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose, and the like.

Tablet binders that can be included are acacia, methylcellulose, sodium carboxymethylcellulose, poly-vinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils, and colloidal silica.

Flavoring agents such as peppermint, oil of wintergreen, cherry flavoring, or the like can also be used. It may be desirable to add a coloring agent to make the dosage form more attractive in appearance or to help identify the product.

For parenteral administration, fluid unit dosage forms are prepared utilizing the compound and a sterile vehicle, with water being preferred. The compound, depending on the vehicle and concentration used, can be either suspended or dissolved in the vehicle. In preparing solutions, the compound can be dissolved in water for injection and filtered sterilized before filling into a suitable vial or ampoule and sealing. Advantageously, adjuvants such as a local anesthetic, preservative, and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the antibiotic.

Additionally, a rectal suppository can be employed to deliver the compound. This dosage form is of particular interest where the mammal cannot be treated conveniently by means of other dosage forms, such as orally or by insufflation, as may be the case of animals, or young children, or debilitated persons. The antibiotic can be incorporated into any of the known suppository bases using methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 gm.

The term "unit dosage form" is defined herein as physically discrete units suitable as unitary dosages for human subjects and animals, each unit containing a predetermined quantity of active material calculated to produce the desired pharmaceutical effect in association with the required pharmaceutical diluent, carrier, or vehicle. The specifications for the novel unit dosage forms of the invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

Typically, any effective quantity of a compound of the present invention is employed in treatment. The determination of an appropriate dosage of the compound for a given treatment depends on many factors that are well known to those skilled in the art. They include for example, the route of administration and the potency of the particular compound.

The particular compound may be present in the composition as the sole therapeutic agent or may be present together with other therapeutic agents, either related or unrelated to the original compound.

A convenient method of practicing the treatment method may be to administer a compound of the present invention via intravenous infusion. In this procedure a sterile formulation of a suitable soluble salt of the compound is incorporated in a physiological fluid, such as 5% dextrose solution, and the resulting solution is infused slowly IV. Alternatively, the piggy-back method of IV infusion can also be used. For intravenous IV use, a water soluble form of the antibiotic can be dissolved in one of the commonly used intravenous fluids and administered by infusion. Such fluids as, for example, physiological saline, Ringer's solution, or 5% dextrose solution can be used.

For intramuscular preparations, a sterile formulation of a suitable soluble salt form of the compound, for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, for example, an ester of a long chain fatty acid such as ethyl oleate.

A composition comprising a compound of the present invention can be administered in a single daily dose or in multiple doses per day. The treatment regimen may require administration over extended periods of time, for example, for several days or for from one to six weeks. The amount per administered dose or the total amount administered will depend on such factors as the nature and severity of the infection, the age and general health of the patient, the tolerance of the patient to the antibiotic and the microorganism or microorganisms involved in the infection.

Catheter infections may lead to severe complications for a patient, and, even if they are not life-threatening, they may contribute to a prolongation of hospital stay and to an increase in therapy costs. Most of the catheter infections can be managed by removing the catheter if clinical signs of infection occur; this is normal clinical routine procedure in patients having short peripheral venous lines. Gram-positive bacteria like *Staphylococcus aureus* and coagulase negative staphylococci (CNS) are the predominant causative organisms.

A further object of the present invention is a method of preventing catheter related infections in a patient in need of application of a central venous catheter, such method consisting in the insertion into the patient of a central venous polyurethane catheter with a thin hydrophilic layer on the surfaces loaded with a compound of the present invention. Central venous polyurethane catheters with a thin hydrophilic layer on the surfaces loaded with a compound of the present invention, may be effective in inhibiting development of bacterial colonization and preventing catheter related infections after the insertion into the patients. The present invention provides a central venous polyurethane catheter with a thin hydrophilic layer on the surfaces loaded with a compound of the invention, in a concentration sufficient to inhibit the bacterial colonization of the catheter after its insertion into the patient. Catheters particularly suitable for use in the invention are polyurethane catheters with a thin hydrophilic coating on both the internal and external surface based on a poly-N-vinylpyrrolidone-polyurethane interpolymer of approximately 200 micron thickness. The catheters of the invention can be maintained in place for the desired period without incurring severe complications for the catheterized patient.

Compositions as described may be used for the treatment of infections of inter alia, the respiratory tract, the urinary tract, and soft tissues in humans. The compositions may also be used to treat infections of domestic animals such as mastitis in cattle.

Provided, then, are compositions and methods of treating bacterial infection in an organism, such as a plant or mammal, which comprises administering to the organism an antibacterially effective amount of a munumbicin or kakadumycin, or a salt or ester thereof. The compositions can be used to control parasitic organisms, including, but not limited to, infections caused by Gram positive bacteria and also some Gram negative bacteria. In a preferred aspect, the compositions are useful in the control of a parasitic *Plasmodium* spp., for example, *Plasmodium falciparum* or *Plasmodium vivax*, which comprises administering to an infected human an effective amount of a munumbicin or kakadumycin, or a salt or ester thereof.

The compositions can also be used to control bacterial pathogens. Pathogenic bacterial organisms which may be controlled by the compositions include, but are not limited to, strains of *Escherichia coli, Shigella dysenteriae, Klebsiella pneumoniae, Pseudomonas aeruginosa, Pseudomonas syringae, Burkholderia cepacia, Acinetobacter boumanii, Neisseria gonorrhoeae, Haemophilus influenzae, Stenotrophomas maltophilia, Staphylococcus* spp., *Staphylococcus aureus, Staphylococcus aureus* MRSA, *Staphylococcus aureus* GISA, *Streptococcus pneumoniae, Enterococcus* spp., *Enterococcus faecalis, Enterococcus faecalis* VRE, *Enterococcus faecium, Mycobacterium* spp., *Mycobacterium tuberculosis, Bacillus anthracis, Erwinia carotovora, Vibrio fischeri, Streptococcus* spp., and *Acinetobacter* spp.

Also provided are compositions and methods of treating fungal infection in an organism, such as a plant or mammal, which comprises administering to the organism an antifungal, effective amount of a munumbicin or kakadumycin, or a salt or ester thereof.

The compositions can also be used to control diverse fungal pathogens including, but not limited to, *Pythium ultimum, Rhizoctonia solani, Aspergillus* spp., *Aspergillus fumigatus, Fusarium oxysporum, Botrytis alli, Alternaria helianthi, Phytophthora infestans, Penicillum* sp., *Sclerotinia sclerotiorum, Cryptococcus neoformans, Histoplama capsulatum, Blastomyces dermatitidis, Cochliobolus carbonum, Geotrichum candidum, Phytophthora cinnamomi, Rhizoctonia solani, Candida tropicalis, Candida globrata,* and *Candida albicans, Candida tropicalis,* and *Candida parapsilosis.*

The compositions can also be used to protect against viral pathogens, or against an array of invertebrate pathogens.

The compositions can also be used in the treatment of cancer. Such cancer cells include, but are not limited to, human lung cancer epithelial A549 cells, human cervical cancer epithelial ME180 cells, and human breast cancer epithelial BT-20 cells.

In a further aspect, the present invention provides a method for treating infectious diseases, especially those caused by Gram-positive microorganisms, in animals. The compounds of the preesent invention are particularly useful in treating infections caused by *Staphylococcus, Enterococcus,* and *Streptococcus* species. Also, the compounds are useful in treating infection due to *Listeria monocytogenes, Vibrio fischeri,* and *Bacillus anthracis.* Examples of such diseases are community acquired pneumonia, nosocomial infections such as ventilator associated pneumonia, and bacterimia. The animal may be either susceptible to, or infected with, the microorganism. The method comprises administering to the animal an amount of a compound of the present invention which is effective for this purpose. In general, an effective amount is a dose between about 0.5 and about 100 mg/kg. A preferred dose is from about 1 to about 60 mg/kg of active compound. A typical daily dose for an adult human is from about 50 mg to about 5 g.

Compounds derived from endophytic *Streptomyces* spp. may also be used to promote growth in meat-producing animals such as broiler chicks, swine, and cattle. The determination of the appropriate amounts and procedures for the use of the antibiotics of the present invention to promote growth in meat-producing animals would be well-known to one of ordinary skill in the art.

The compositions of the invention may be pesticidal compositions used for administration to plants, or the associated soil. For use with a plant, the method may involve applying an endophytic Streptomycete strain, or an extract or compound derived from the strain either directly to the plant, or to soil adjacent to the plant. In some cases the treatment may be made to seeds. In certain circumstances, the strain can be applied to grow in association with the plant and produce the biologically active compounds capable of protecting the plant against plant pathogen attack.

The present invention is further directed to pesticidal compositions comprising the substance in an effective amount to control a pest and a pesticidal carrier. "Effective amount" is defined herein as the amount of the substance sufficient to control a pest through killing or stunting of the growth of the pest or protecting a plant from pest infestation. The pesticidal compositions may comprise a compound of the present invention in a substantially pure form or as an extract from a whole broth culture of an endophytic Streptomycete in dry, concentrated, or liquid form and a suitable pesticidal carrier, examples of which are disclosed infra. The substance is present in the composition at a concentration of from about 0.001% to about 60% (w/w).

The pesticidal compositions may further comprise a deposition agent which assists in preventing the composition from drifting from the target area during application (e.g., as it is sprayed from a plane), or from being blown away from the plant once it has been deposited. The deposition agent in the compositions of the present invention is preferably a proteinaceous material, which has the added benefit of being palatable to the insect. Any animal or vegetable protein is suitable for this purpose, in dry or in liquid form. Examples of useful sources of protein which can be conveniently and economically added to the composition include, but are not limited to, soy protein, potato protein, soy flour, potato flour, fish meal, bone meal, yeast extract, and blood meal. Alternative deposition agents include modified cellulose (carboxymethylcellulose), botanicals (grain flours, ground plant parts), non-phyllosilites (talc, vermiculite, diatomaceous earth), natural clays (attapulgite, bentonite, kaolinite, montmorillonite), and synthetic clays (Laponite). When utilized, the deposition agent is present in the pesticidal compositions of the present invention in an amount of between about 0.4% w/w and about 50% w/w, preferably between about 1% w/w and about 20% w/w.

The pesticidal compositions may further comprise an antifreeze/humectant agent which suppresses the freeze point of the product and helps minimize evaporation when sprayed and which maintains deposit texture making the product more efficacious and palatable. Examples of antifreeze/humectant agents include, but are not limited to, ethylene glycol, propylene glycol, dipropylene glycol, glycerol, butylene glycols, pentylene glycols and hexylene glycols. When utilized, the antifreeze/humectant agent is present in the pesticidal compositions of the present invention in an amount of between about 0.5% w/w and about 25% w/w, preferably between about 2% w/w and about 15% w/w.

The pesticidal compositions may further comprise a surfactant in an amount where it acts as an emulsifying, a wetting, or a dispersing agent. Examples of such surfactants are anionic surfactants such as carboxylates, for example, a metal carboxylate of a long chain fatty acid; N-acylsarcosinates; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl naphthalene sulphonate; salts or sulphonated naphthalene-formaldehyde condensates; salts of sulphonated phenol-formaldehyde condensates; or more complex sulphonates such as amide sulphonates, e.g., the sulphonated condensation product of oleic acid and N-methyl taurine or the dialkyl sulphosuccinates, e.g., the sodium sulphonate or dioctyl succinate. Further examples of such surfactants are non-ionic surfactants such as condensation products of fatty acid esters, fatty alcohols, fatty acid amides or fatty-alkyl- or alkenyl-substituted phenols with ethylene oxide, block copolymers of ethylene oxide and propylene oxide, acetylenic glycols such as 2,4,7,9-tetraethyl-5-decyn-4,7-diol, or ethoxylated acetylenic glycols. Further examples of such surfactants are cationic surfactants such as aliphatic mono-, di-, or polyamine as acetates, naphthenates or oleates; oxygen-containing amines such as an amine oxide of polyoxyethylene alkylamine; amide-linked amines prepared by the condensation of a carboxylic acid with a di- or polyamine; or quaternary ammonium salts. When utilized, the surfactant is present in an amount of between about 0.5% w/w and about 25% w/w, preferably between about 1% w/w and about 8% w/w.

The pesticidal compositions may further comprise an inert material. Examples of inert materials include inorganic minerals such as diatomaceous earth, kaolin, mica, gypsum, fertilizer, phyllosilicates, carbonates, sulfates, or phosphates; organic materials such as sugars, starches, or cyclodextrins; or botanical materials such as wood products, cork, powdered corncobs, rice hulls, peanut hulls, and walnut shells.

The pesticidal compositions may further comprise a preservative, a feeding stimulant, an attractant, an encapsulating pesticide, a binder, a dye, an ultraviolet light protectant, a buffer, a flow agent, or other component to facilitate product handling and application for particular target pests.

The pesticidal compositions can be applied in a dry or liquid form, e.g., a suspension, a solution, an emulsion, a dusting powder, a dispersible granule, a wettable powder, an emulsifiable concentrate, an aerosol or impregnated granule, or a concentrate or primary composition which requires dilution with a suitable quantity of water or other diluent before application. The concentrations of each component in the composition will vary depending upon the nature of the particular composition, specifically, whether it is a concentrate or to be used directly. The composition may contain about 1% to about 98% of a solid or liquid inert carrier. The compositions will be preferably administered at the labeled rate for commercial products, preferably about 0.01 pound to 5.0 pounds per acre when in dry form and at about 0.01 pint to 25 pints per acre when in liquid form.

The pesticidal compositions can be applied directly to a plant by, for example, spraying or dusting at the time when the pest has begun to appear on the plant or before the appearance of pests as a protective measure. The pesticidal compositions can be applied by foliar, furrow, broadcast granule, "lay-by", or soil drench application. The compositions can also be applied directly to ponds, lakes, streams, rivers, still water, and other areas subject to infestation by pests of concern to public health. The compositions can be applied by spraying, dusting, sprinkling, or the like. The spray or dust can conveniently contain another pesticide. The pesticidal compositions are preferably applied directly to the plant.

The pesticidal compositions can be applied to protect a number of different plant types, including, but not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes), lauraceae (avocados, cinnamon, camphor), deciduous trees and conifers (linden-trees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamentals.

The present invention is further described by the following examples, which should not be construed as limiting the scope of the invention.

EXAMPLES

Materials

All solvents used for HPLC were HPLC grade. Those used for extraction were ACS grade. All other reagents were obtained from Sigma Chem. Co., St. Louis, Mo., including adrenocorticotropic hormone fragment 18-39, standard amino acids, and radiolabelled phenylalanine.

Example 1

Isolation and Identification of the Endophytes of *Kennedia nigriscans*

Stems (0.5-1.0 cm is diameter) of *Kennedia nigriscans* were obtained near the Aboriginal village of Manyallaluk, southeast of Katherine, Northern Territory, Australia at 14° 16' 33" South and 132° 49' 45" East. The stems were thoroughly treated with 70% ethanol and then the outer bark removed with a sterilized sharp blade. The inner pieces of the stem, containing the cambium, phloem, and xylem tissues, were plated on water agar in Petri plates. After incubation for at least 7-10 days at 23° C., individual fungal and bacterial colonies were removed with a sterile fine tipped needle and transferred onto potato dextrose agar (PDA) composed per liter of 39 g of potato dextrose agar.

The stems of *Kennedia nigriscans* (snakevine) yielded at least 24 endophytic microorganisms (FIG. 1). At least three of these were *Pestalotiopsis* spp., which is common for plants growing in tropical or semi-tropical environments (Li et al., 2001). One endophyte, designed A11-4C, showed strong antimicrobial activity. This organism resembled a *Streptomyces* sp. and was not isolated as an endophyte from any plants in the near vicinity of *K. nigriscans*, including *Banksia dentata* and *Owenia vernisoa*.

The putative Streptomycete was grown on gamma-irradiated carnation leaves as well as autoclaved freshly harvested snakevine after placement on water agar. After 10-14 days the cultures were examined for the production of fruiting structures. On carnation leaves, only little or modest spore production occurred (FIG. 2). However, on the inoculated natural host of this microbe, snakevine, there was the production of numerous spiral and curved mycelia, some having chains of many spores (FIG. 3). This observation pointed to the prospect that this endophytic microorganism had developed some biochemical relationship with its host plant since it so readily made spores on this plant and not on others, such as carnation leaves.

The organism fits, in all respects, the definition of a *Streptomyces* sp. It produced slow growing, erumpent, multisectored, and multicolored colonies on PDA. Whitish mycelia, mixed with areas of spore production that were tan to brownish in coloration occurred primarily in the border regions of 4-5 week old colonies growing on PDA. Toward the center and in mid-sections of the colony appeared greasy yellowish-orange raised areas.

Fruiting structures of the microorganism appearing on both carnation leaves and the tissues of the host plant were examined by stereo and light microscopy. These structures were fixed and processed using the standard methods of fixation (Worapong et al., 2001) by placement in 2% (v/v) glutaraldehyde in 0.1 M sodium cacodylate buffer (pH 7.2) and left overnight. The samples were then passed through a gradient of ethanol solutions to discourage the processes of shriveling which normally occurs in spores and mycelia with rapid dehydration. The samples were then critical-point dried, gold coated with a sputter coater, and observed and photographed with a JEOL 6100 scanning electron microscope.

An examination of the organism by scanning electron microscopy revealed the presence of numerous aerial filaments, and smooth, cylindrical spores, (0.8 micron in length and 0.7 micron in diameter) that were being produced in long curved as well as spiral chains (FIGS. 2 and 3). Cultures growing on PDA, after 4-5 weeks, began to exude a water-soluble pigment that diffused into the medium giving a distinctive reddish-orange coloration around the individual colonies. In older cultures, reddish droplets appeared on the mycelium. These droplets were individually collected and dried. After chromatographic separation, munumbicins were the primary compounds present, having a yellowish to reddish-orange coloration, depending on the concentration and the compound(s) present.

Example 2

Isolation of Other Biologically Active Endophytic Streptomycetes

The procedure described in Example 1 for selecting endophytic *Streptomyces* spp. was applied to other plants. Plates were continuously monitored for spore formation by stereo and light microscopy. In some cases, individual Streptomycete colonies were obtained only after 2-3 weeks, because of their small size. They also tended to have close proximity to the plant material and care was needed to obtain them in a pure culture. In other cases they were located beneath the plant material that was placed on the water agar plate. Because of the extended incubation time and their small size, these colonies were easily overlooked.

Using the methodology described, it was possible to acquire a number of other *Streptomyces* spp. Each of these was shown by microscopic techniques to be a Streptomycete primarily based on small spore size and the occurrence of spores in chains. In addition each of these has been cultured as described above and shown via bioassay techniques to have antifungal and antibacterial activities. These Streptomycetes have been acquired from higher plants around the world and have potential as a biological source of novel useful products. Other representative biologically active *Streptomyces* spp. obtained from higher plants as endophytes by these methods are provided below in Table 1.

TABLE 1

| Plant Source | Country of Origin and lab designation number | Antibiotic Activity* |
|---|---|---|
| *Taxus wallichana* | Nepal (No. 303; No. 305; No. 307) | +++ |
| *Theobroma cacao* | Peru (P2-17) | ++ |
| *Grevillia pteridifolia* | Australia (A3-5-1) | ++++++ |
| *Dunalia purpurea* | Peru (P-2-24) | ++ |
| *Monstera speciosa* | Peru (P-25) | +++ |

*Denotes the relative antibiotic activity of the concentrated culture extract with + being low and +++++ being the highest.

Each *Streptomyces* sp. was grown for two weeks on a Petri plate of potato dextrose agar and subsequently and independently challenged with the test organisms *Pythium ultimum* and *Geotrichum candidum*. Zones of inhibition that were noted after two days were recorded and given the relative scores of (+) based on the degree of inhibition.

Biologically active endophytes were deposited in the MSU culture collection, as numbers 2110 (P-25), 2111(303), 2112 (P2-17), 2113 (A3-5-1), and 2114 (P2-24). They were also deposited with the Agricultural Research Service Patent Culture Collection, as NRRL 30563, NRRL 30564, NRRL 30565, NRRL 30566, and NRRL 30567, each with a deposit date of Mar. 12, 2002. The strain designated *Streptomyces munumbi* (A3-5-1) was deposited with the Agricultural Research Service Patent Culture Collection as NRRL 30562 with a deposit date of Mar. 7, 2002, and MSU collection number 2101.

Example 3

Isolation Procedures for the Munumbicins

Small blocks of PDA containing *Streptomyces munumbi* were inoculated into 500 ml of PD broth (39 g of potato dextrose per liter) in a 2 liter Erlenmeyer flask and incubated for 3 weeks at 23° C. without shaking. The culture filtrate was then extracted three times with ½ volumes of methylene chloride. The extracts were pooled and then taken to dryness under flash evaporation at 40° C. The yield of dry material per liter was about 250 mg. Approximately 5 mg of the material was subjected to high pressure liquid chromatography (HPLC) on a Microsorb 60-8 Dynamax C-18 column, 250×10 mm (5 micron). The elution solvent was 20% tetrahydofuran (THF):80% water programmed for 60 minutes to a final concentration of 40% THF:60% water and then held isocratically for 95 minutes. The elution stream was continuously monitored at 260 nm with a flow rate of 2 ml/minute.

Individual fractions were subjected to a bioassay test by placing them on a Petri plate with PDA, drying, and then challenging with small blocks of agar containing *Pythium ultimum*. The fractions were considered active if inhibition of fungal growth was observed. Each fraction was repurified using the same HPLC system and these fractions were weighed and primarily used for bioassay tests. The compounds in the fractions were at least 95% pure. Final purification for spectroscopic measurements was made by subjecting each compound to HPLC on a Microsorb 100-5 C-18 column, 250×4.6 mm. The initial elution solvent was 20% acetonitrile: 80% water for 90 minutes programmed to a final concentration of 80% acetonitrile. The retention time of each peak was recorded and the bioactivity of each peak was determined.

Example 4

Bioassays for the Munumbicins

The bacterial isolates used for the majority of the disk bioassays were obtained from the American Type Culture Collection (ATCC). After primary isolation on the media recommended by ATCC, organisms from a single colony were cultured overnight in 10 ml Mueller-Hinton Broth (MHB) (Benton, Dickinson, and Co., Sparks, Md.) at 35° C. unless otherwise specified with or without 5% $CO_2$. After 12 hours incubation, 0.5 ml of the bacterial suspension was added to 4.5 ml of pre-warmed MHB and the solution was incubated at 35° C. to obtain cultures in the logarithmic phase of growth. The inoculum for the bacterial disk diffusion assays was prepared as described in the protocols of the U.S. National Committee for Clinical Laboratory Standards manual (NCCLS; 940 West Valley Road, Wayne, Pa.). Compounds to be tested including known antibiotics were dissolved in 2-10% methanol and applied to sterile (6 mm diameter) paper disks, dried and then applied to the appropriate medium for testing. The plate medium used for testing the disks was MHA for all isolates except *Neisseria gonnorheae* and *Streptococcus pneumoniae* for which GC agar base with 1% defined growth supplement and MHA with 5% defibrillated sheep's blood, respectively, were used according to the NCCLS manual. Incubation conditions were 35° C. overnight unless otherwise specified with or without 5% $CO_2$ as recommended.

Microbroth dilution assays of human associated bacteria and fungi were performed as described in the NCCLS manual. The bacteria were obtained from the ATCC and each of the fungi tested were from the microbial collection at Eli Lilly (Indianapolis, Ind.) where the tests were conducted. The assays were performed in sterile 96 well plates, and the total volume per well was 100 microliters. The bacterial inoculum was prepared to provide approximately $10^4$ to $10^5$ colony forming units per well and the compounds were tested at concentrations from 0.0625 to 64 micrograms/ml in two-fold step dilution. The actual colony forming units per well was confirmed by plating onto TSB or blood agar. Two wells were inoculated for a given concentration. The plates were incubated for 16 to 20 hours at 35° C. unless otherwise specified with or without 5% $CO_2$ Plant associated microorganisms were tested for their response to the munumbicins using a microbroth (potato broth-PD) dilution technique carried out in 24 well-dilution plates using several 3 $mm^3$ agar blocks containing fungal inoculum placed in 1 ml of PD broth. Incubation was for 48 hours at 23° C. A plant pathogenic strain of *Pseudomonas syringae* was also tested using the same PD broth medium and with concentrations of colony forming units as given above. The organisms were obtained from the Montana State University plant pathogen culture collection administered by Dr. Don Mathre.

Each of the munumbicins demonstrated biological activity against an array of plant pathogens, even at low MIC values. The relative activities against plant pathogenic fungi ranged from a few tenths of a microgram up to thirty micrograms. Table 2 provides the results of tests of inhibitory activity of the munumbicins against various plant-pathogenic fungi and one pathogenic bacterium. The data are reported as MIC values in micrograms/ml.

TABLE 2

| Test organism | Munumbicin A micrograms/ml | Munumbicin B micrograms/ml | Munumbicin C micrograms/ml | Munumbicin D micrograms/ml |
|---|---|---|---|---|
| *Pythium ultimum* | 2.0 | 0.2 | 4.0 | 0.4 |
| *Rhizoctonia solani* | — | 8.0 | 1.5 | 15.6 |
| *Phytophthora cinnamomi* | — | 6.2 | 1.5 | 15.6 |
| *Geotrichum candidum* | — | 31.2 | 15.6 | 31.2 |
| *Sclerotinia sclerotiorum* | 8.0 | 0.20 | 8.0 | 2.0 |
| *Pseudomonas syringae* | 15.6 | 2.0 | 15.6 | 0.2 |

"—" = activity not determined.

The least active munumbicin, based on the comparative MIC values, appeared to be munumbicin D, while the other munumbicins generally possessed lower MIC values against these microorganisms. The fact that these compounds had such remarkable activity against plant pathogenic fungi and at least one bacterium suggests that *Streptomyces munumbi*, as an endophyte, may have some role to play in providing protection to the host plant from invading pathogen.

Example 5

*Streptomyces munumbi* as a Biological Control Agent

Comparisons were made between *Streptomyces munumbi* and *Streptomyces griseoviridis* which is included in the formulation for "Mycostop", a commercial agricultural product of Butts International Inc., Fairfield, Conn., USA, which is used to control *alternaria, fusarium*, and *phomopsis* caused diseases in plants.

Cultures of both organisms were grown for 7-10 days using the procedure described in Example 3 and then challenged with plant pathogens for a 4 day incubation period on plates of PDA. Zones of inhibition were measured and compared. There were comparable effects between the two Streptomycetes with *Rhizoctonia solani, Aspergillus* sp., *Fusarium oxysporum, Botrytis alli*, and *Alternaria helianthi*. However, the zones of inhibition were nearly twice as great with *Streptomyces munumbi* as the *Streptomyces griseoviridis* with such organisms as *Pythium ultimum, Phytophthora infestans, Penicillum* sp., *Sclerotinia sclerotiorum, Erwinia carotovora*, and *Cochliobolus carbonum*. It appears that *Streptomyces munumbi* has the potential to be considered for

*development as an agricultural agent especially as it relates to the control of plant diseases either in or on plants or possibly in soils infested with them.*

Example 6

*Streptomyces munumbi* Against Human Pathogens

A general disk screening test was applied to a series of human pathogenic bacteria as described in Example 4. The diameter of the zone of inhibition was taken as a relative indication of biological activity of the various munumbicins. Most notable from this testing regimen was the fact that each of the Gram positive bacteria tested was sensitive to one or more of the munumbicins. Table 3 shows the inhibitory activity of the munumbicins and some standard antibiotics against various bacteria in a disk diffusion assay conducted on Muller Hinton broth agar medium at 35° C., unless otherwise noted.

TABLE 3

| Bacterium tested* | Mun. A mm | Mun. B mm | Mun. C mm | Mun. D mm | Ciprofloxacin mm | Vancomycin mm | Chloramphenicol mm | Penicillin mm |
| --- | --- | --- | --- | --- | --- | --- | --- | --- |
| *Pseudomonas aeruginosa* ATCC 27853 | R | R | R | R | 30 | — | — | — |
| *Vibrio fischeri* PIC 345 | R | 16 | 9 | 12 | | | — | — |
| *Enterococcus faecalis* ATCC 29212 | R | 18 | 20 | 16 | — | 18 | — | — |
| *Enterococcus faecalis* ATCC 51299 | R | 23 | 22 | 16 | 22 | — | — | — |
| *Staphylococcus aureus* ATCC 29213 | R | 15 | R | 13 | — | 15 | — | — |
| *Acinetobacter* sp. ATCC 49137 grown at 30° C. | R | R | R | R | 29 | — | — | — |
| *Neisseria gonnorhea* ATCC 49226# | 9 | 14 | 8 | 9 | — | 13 | — | — |
| *Streptococcus pneumoniae* ATCC 49619• | R | 17 | 7 | 16 | — | 20 | — | — |
| *Bacillus anthracis* K8902 | 9.5 | 18 | R | — | 16 | — | — | — |
| *Escherichia coli* ATCC 25922† | R | R | R | R | — | — | — | — |
| *S. epidermis* ATCC 12228 | 9 | 21 | R | 14 | — | — | — | — |
| *S. maltophilia* ATCC 13637 | R | 9 | R | R | — | — | — | — |
| *Shigella dysenteriae* ATCC 11835 | R | R | R | R | — | — | 11 | — |
| *Enterococcus faecium* ATCC 49624 | — | 21 | 23 | — | 15 | 22 | 24 | 21 |
| *Enterococcus faecium* ATCC 51559 | — | 26 | 28 | — | 13 | 0 | 24 | 0 |
| *Candida albicans* ATCC 24433 | R | R | R | R | — | — | — | — |
| *Candida albicans* ATCC 90028 | R | R | R | R | — | — | — | — |
| *Candida parasilosis* ATCC 22019 | R | R | R | R | — | — | — | — |
| *Candida tropicalis* ATCC 750 | R | R | R | R | — | — | — | — |
| *Candida krusei* ATCC 6258 | R | R | 8 | R | — | — | — | — |
| *Candida glabrata* ATCC 2001 | R | R | R | R | — | — | — | — |
| *Candida parasdosis* | R | R | R | R | — | — | — | — |

TABLE 3-continued

| Bacterium tested* | Mun. A mm | Mun. B mm | Mun. C mm | Mun. D mm | Ciprofloxacin mm | Vancomycin mm | Chloramphenicol mm | Penicillin mm |
|---|---|---|---|---|---|---|---|---|
| ATCC 90018 *Cryptococcus neoformans* ATCC 32045 | — | 12 | 12 | — | — | — | — | — |
| *Saccharomyces cerevisiae* ATCC 9763 | — | R | R | — | — | — | — | — |

— = not determined
R = resistant
*Number located beside the bacterial name indicates the ATCC or Presque Isle (PIC) acquisition number.
GC agar with 1% growth supplement with 5% $CO_2$.
• MHA with 5% dsb. and 5% $CO_2$.
† Resistant to penicillin G applied at 10 units per disk.

The test compound was administered on sterile paper disks at 10 micrograms per disk while ciprofloxacin and vancomycin were administered at 5 and 30 micrograms per disk, respectively. The developing zone of inhibition was measured and reported as the diameter of the zone of inhibition. Details of the culture conditions are given above.

*Streptomyces munumbi* was active against such important pathogenic bacteria as *Bacillus anthracis, Streptococcus pneumoniae, Enterococcus faecalis* and *Staphylococcus aureus*. In fact, two of the Gram positive munumbicin sensitive bacterial strains are common drug resistant ATCC strains. This includes a methicillin-resistant strain of *Staphylococcus aureus* (ATCC 33591) and a vancomycin resistant strain of *Enterococcus faecalis* (ATCC 51299). Table 4 shows the minimum inhibitory concentrations (MICs) of the munumbicins against various human pathogenic fungi and bacteria. The data are reported as micrograms/ml.

TABLE 4

| Test organism | Mun. A micrograms/ml | Mun. B micrograms/ml | Mun. C micrograms/ml | Mun. D micrograms/ml | Amphotericin B micrograms/ml |
|---|---|---|---|---|---|
| *Cryptococcus neoformans* | 10 | 10 | 10 | 10 | 0.13 |
| *Candida albicans* | — | — | >10 | >10 | 1.25 |
| *Aspergillus fumigatus* | 20 | 20 | 20 | 20 | 0.62 |
| *Staphylococcus aureus* ATCC 33591‡ | N.A. | 2.5 | N.A. | N.A. | — |
| *Staphyloccus aureus* MH II Eli Lilly Co.† | — | — | 0.4 | 0.4 | — |
| *Enterococcus faecalis* ATCC 51299≠ | 8 | N.A. | 16 | N.A. | — |
| *Bacillus subtilis* | — | 8 | >8 | — | — |
| *E. faecalis* 51299 | — | 8 | — | — | — |
| *Bacillus subtilis* | — | 2 | 0.25 | — | — |
| *S. epidermis* 12228 | — | 1 | 2 | — | — |
| *E. faecium* 49624 | — | 0.5 | 0.5 | — | — |
| GISA 700699 | — | 2 | 2 | — | — |
| *E. faecalis* VRE 51299 | — | 0.5 | 0.5 | — | — |
| *E. faecalis* 29212 | — | 0.25 | 0.5 | — | — |
| *S. aureus* 29213 | — | 0.5 | 1 | — | — |
| MRSA 33591 | — | 0.5 | 0.5 | — | — |
| *Bacillus cereus* 4342 | — | 0.5 | 0.25 | — | — |
| *Listeria monocytogenes* 19114 | — | 4 | 4 | — | — |
| *Listeria monocytogenes* 19115 | — | 4 | 2 | — | — |

TABLE 4-continued

| Test organism | Mun. A micrograms/ml | Mun. B micrograms/ml | Mun. C micrograms/ml | Mun. D micrograms/ml | Amphotericin B micrograms/ml |
|---|---|---|---|---|---|
| *Staphylococccus simulans* 11631 | — | 1 | 1 | — | — |
| *Staphylococccus aureus* 27734 | — | 0.5 | 0.5 | — | — |
| *Streptococcus pneumoniae* 49619 | — | 0.5 | 0.125 | — | — |
| *Streptococcus pneumoniae* 700674 | — | 0.5 | 0.125 | — | — |
| *Streptococcus pneumoniae* 700676 | — | 0.5 | 0.125 | — | — |

N.A. = not active at all concentrations tested.
— = activity not determined
‡ = methicillin resistant strain
† = sensitive to vancomycin MIC = 0.06 micrograms/ml
≠ = resistant to vancomycin and sensitive to ciprofloxacin

*Enterococcus faecalis* (ATCC 51299) was sensitive to ciprofloxacin (Table 3). Also, it appeared that many of the Gram negative bacteria were resistant to the munumbicins at the concentration applied on the disk and then to the assay plate (Table 3). This includes representative bacteria such as *E. coli, Acinebacter* sp., and *Pseudomonas aeruginosa*. However, in the latter case, the human pathogenic pseudomonad appeared to be resistant to all of the munumbicins, whereas a plant pathogenic pseudomonas was sensitive (Table 2).

The results of the disk tests led to the more refined method of determining the relative effectiveness of antibiotics—the MIC test against some of the drug sensitive bacteria and fungi pathogenic on humans. Ultimately, values of 2.5 micrograms/ml and 12.5 micrograms/ml were observed for munumbicin B against drug resistant *Staphylococcus aureus* and *Enterococcus faecalis*, respectively (Table 4). In this MIC test, the other munumbicins were inactive against these bacteria at the concentrations tested (Table 4). However munumbicins C and D had bioactivity (0.4 micrograms/ml) against a drug sensitive strain of *Staphylococcus aureus* (Table 4). Although the munumbicins were quite active against plant pathogenic fungi, their activity against human pathogenic fungi was less impressive with MIC values that did not reach below 10 micrograms/ml, which is in marked contrast to the striking effects of amphotericin B to these organisms (Table 4).

Example 7

Inhibitory Concentrations ($IC_{50}$'s) for Munumbicins with *Mycobacterium tuberculosis*

$IC_{50}$'s were determined for multiple-drug-resistant *Mycobacterium tuberculosis* (MDR-P) and a standard drug sensitive strain (H37Rv, ATCC 25618) of this organism. A modified procedure commonly used to test slow growing bacteria was used to determine the effectiveness of the munumbicins against these bacteria (Isenberg, 1992). The test compounds were dissolved in DMSO and appropriately diluted and placed in *Mycobacteria* 7H11 agar (Becton, Dickinson, and Co., Sparks, Md.) supplemented with 10% OADC (oleic acid-albumin-dextrose-catalase) enrichment. All experiments were carried out in a biosafety level-3 facility. The $IC_{50}$'s were calculated by linear regression analysis after the relative % growth of cultures was compared to control cultures. This experiment was repeated twice.

One of the most interesting activities of the munumbicins is munumbicin B against multiple-drug-resistant (MDR-P) *Mycobacterium tuberculosis*, an acid-fast bacterium. Munumbicin B had an $IC_{50}$ value of 10 micrograms/ml whereas rifampicin was virtually inactive against this organism, even at elevated concentrations. Table 5 shows the effects of the munumbicins against drug resistant and a common drug sensitive strain of *Mycobacterium tuberculosis*. The data are reported as the $IC_{50}$ values in micrograms/ml and were obtained from plots of treated recoverable *Mycobacterium tuberculosis* as a function of concentration of drug administered to the culture.

TABLE 5

| Compound Tested | *M. tuberculosis* MDR-P (drug resistant) micrograms/ml | *M. tuberculosis* H37Rv (ATCC 25618) (drug sensitive) micrograms/ml |
|---|---|---|
| Munumbicin B | 10 | 46 |
| Munumbicin C | >125 | >150 |
| Rifampicin | >150 | <1 |

Only the MDR-P strain of *Mycobacterium tuberculosis* was sensitive to munumbicin B whereas the drug susceptible strain of this organism was not as sensitive to munumbicin B (Table 5).

Example 8

Antimalarial Assay for the Munumbicins

Cultures of *Plasmodium falciparum* strain CSC-1 (Honduras) were maintained according to the methods of Trager and Jensen, 1976; and Trager and Jensen, 1978, except that human serum was replaced with Albumax I (Gibco, BRL); 6% w/v stock solution in RPMI 1640 medium (Trager and Jensen, 1976; Trager and Jensen, 1978) containing 0.1 mg/ml hypoxanthine stored at −20° C. All cultures were maintained in a microaerophilic environment containing 1% oxygen/5% $CO_2$ with the balance being nitrogen. The stock solution was diluted at a ratio of 5:100 v/v of RPMI 1640 to give a final concentration of 0.3% Albumax I. Stock solutions of the compounds to be tested, including the munumbicins and choloroquine, were initially dissolved in DMSO or water and diluted to final concentrations in Albumax-supplemented RPMI 1640 medium. Control cultures contained the same quantity of DMSO or water as that used in the experimental trials.

Parasite cultures, adjusted to 0.1-0.5% parasitemia by addition of freshly washed human erythrocytes, were pipetted into 96 well culture plates by adding 10 microliters of a 50% cell suspension to each well to give a final volume of 5 microliters of packed erythrocytes per well. The test compounds in RPMI 1640 were added at 95 microliters per well to four wells per each concentration of test compound. Quadruplicate control wells were treated similarly with DMSO or water added without the test compounds present. The cultures were gassed and exposed to radiolabeled $^3$[H]-phenylalanine (1 microcurie per well) for the final 24 hour of treatment. Cultures were monitored for bacterial contamination and for parasite viability by Giemsa staining of thin films. Ultimately, the cells were harvested onto glass-fiber filters, followed by liquid scintillation counting. The $IC_{50}$ for each compound was determined by linear regression analysis using 50% of the control counts as the regression point. The experiment was repeated three times, the data averaged, and the standard deviation of the mean determined.

Each of the munumbicins showed strong activity against *Plasmodium falciparum*, the most pathogenic agent of malaria. The $IC_{50}$'s of each compound were quite low. Munumbicins C and D were of special interest because of their extremely low $IC_{50}$'s (Table 6). Table 6 shows the activity of the munumbicins and chloroquine against *Plasmodium falciparum* in an in vivo assay using human red blood cells and a radiobioassay involving $^3$H-phenylalanine and *Plasmodium falciparum* (Trager and Jensen, 1976; Trager and Jensen, 1978). The data are reported as $IC_{50}$ values, the concentration of the drug at which 50% of the plasmodia were killed. The values are in ng/ml and the standard deviation of the mean is presented from three separate experiments.

TABLE 6

| Compound Tested | ng/ml |
|---|---|
| Munumbicin A | 175 ± 106 |
| Munumbicin B | 130 ± 70 |
| Munumbicin C | 6.5 ± 2 |
| Munumbicin D | 4.5 ± 0.7 |
| Chloroquine | 7.0 ± 0 |

Munumbicin D yielded an $IC_{50}$ of 4.5±0.7 ng/ml, which is about 50% below that of the chloroquine, the gold standard antimalarial drug. Munumbicin C was within the same range of biological activity as munumbicin D. Furthermore, none of the munumbicins caused any detectable lysis of human red blood cells up to a concentration of 20 micrograms/ml and munumbicins C and D did not cause lysis up to 80 micrograms/ml.

Example 9

Anticancer Cell Line Tests for the Munumbicins

*Pythium ultimum*, a plant pathogenic oomycete, was sensitive to munumbicin preparations and therefore some spectrum of anticancer activity of one or more of the munumbicins was anticipated (Table 2). The relationship between sensitivity to *Pythium ultimum* and sensitivity to one or more human cancer cell lines seemed to be correlated in past as well as the present study (see Tables 2 and 7) (Strobel et al., 1997). Correlation of brine shrimp sensitivity to various compounds also having activities against human cancer cell lines has been noted (Ferrigni et al., 1984). In preliminary brine shrimp assays, the munumbicins A, B, C, and D demonstrated $LC_{50}$'s of 3.3, 8.2, 2.0, and 1.7 micrograms/ml, respectively.

The munumbicins were then tested against three human cancer cell lines (ATCC) and human primary mammary epithelial cells (HMECs) (Clonetics; Biowhittaker, Walkersville, Md.) using a CellTiter 96® Aqueous Non-Radioactive Cell Proliferation Assay kit from Promega (Madison, Wis.). The cell lines were A-549 (lung epithelial carcinoma, ATCC CCL-185), ME-180 (cervical epithelial epidermoid carcinoma, ATCC HTB-33), and BT-20 (breast epithelial cancer, ATCC HTB-19), and were grown in the media recommended by ATCC. The primary mammary cells were cultured as recommended by the manufacturer in mammary epithelial cell growth media (MEGM®). The cells were seeded into 96 well clear flat bottom plates at 1,000-10,000 per well in 25 to 100 microliters of the recommended culture medium. The HMECs, BT-20, A-549, and ME-180 cells were seeded at 2500, 3000, 5000 and 5000 cells per well, respectively.

After seeding, the cells were incubated for five hours at 37° C. before addition of the munumbicins. Two-fold serial dilutions of the munumbicins were made in the culture medium, and a volume equal to that of the seeded cells for each dilution was added to three wells of cells. Each plate also contained some wells with cells plus medium only and some wells with medium only. After addition of the compounds, the plates were incubated at 37° C. for 12 to 48 hours depending on the cell line. The HMECs and BT-20 cell lines were incubated with the munumbicins for 48 and 96-144 hours, respectively. The A-549 and ME-180 cells were incubated for 48 hours.

The proliferation assay was performed using the manufacturer's protocols; a 20:1 solution of MTS and PMS was mixed and 10 to 40 microliters was added to each well depending on the total volume in the wells. The plates were incubated at 37° C. for one to four hours, and the $OD_{490}$ was determined. The OD reading of all wells was corrected for background by subtracting the reading of wells containing medium only. The wells containing cells only were used as a control for 100% viability. The $IC_{50}$ of each compound was defined as the concentration of compound which gave 50% viability and the experiment was repeated three times and the data averaged and the standard deviation of the mean shown.

Human red blood cells were not affected up to 80 micrograms/ml by munumbicins, but other human tissues show adverse effects of the munumbicins. The compounds with the greatest anticancer activity were munumbicins B and C. Munumbicins B and C had $LC_{50}$'s in the range of 0.1-0.14 micrograms/ml against the ME-180 cancer cell line (Table 7). On the other hand, munumbicins B, C, and D had impressively low $LC_{50}$'s against the BT-20 cell line with values ranging from 0.07 to 0.019 micrograms/ml. Thus, while the munumbicins display anticancer activity, the differential activity between normal (HMEC) and cancer cell lines is relatively narrow in some cases and broader in others.

Example 10

Chemical Characterization of the Munumbicins

Amino Acid Analysis

HPLC purified compounds were dissolved in methanol, placed in 6×50 mm glass tubes, dried in vacuo, and then transferred to a hydrolysis vessel (Millipore, Marlborough, Mass., USA; part no. 007603). Approximately 300 microliters of 6 N HCl were added to the vessel which was then alternatively purged with nitrogen and evacuated three times before being sealed under vacuum. Vapor phase hydrolysis was performed by heating at 110° C. for 22 hours. Separation and quantitation of amino acids was carried out on a Beckman Model 6300 Amino Acid Analyzer. Moles of each amino acid were initially determined using molar absorption values derived from amino acid standards. Other details of these analyses, as performed on a peptide antibiotic from another endophytic organism, have been described (Miller et al., 1998). Each analysis was performed at least three times and the averages presented along with the standard deviation of the mean.

Figure 4:
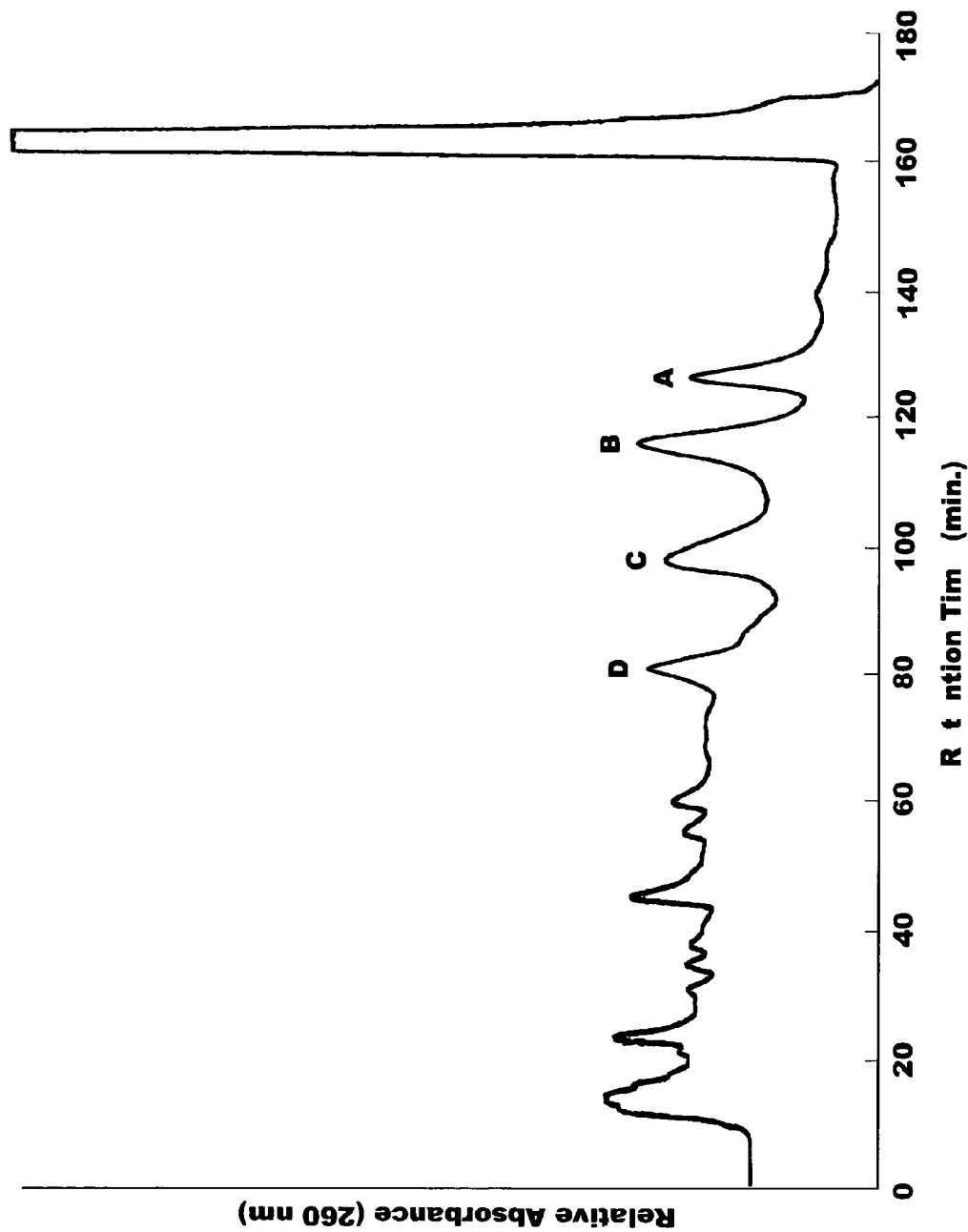
FIG. 4 shows an HPLC elution pattern of the separation of the munumbicins on a Microsorb 60-8 Dynamax C-18 column, 250-10 mm (5 micron). The x axis shows UV absorption at 260 nm while the y axis shows time.

HPLC preparations of the munumbicins were used to chemically characterize these compounds. The major components of the culture medium of *Streptomyces munumbi* appeared as peaks A through D, with varying retention times, after the first passages over a Microsorb 60-8 Dynamax C-18 column, 250×10 mm (5 micron) (FIG. 4). Table 8 provides the yield values along with chromatographic and spectroscopic properties of munumbicins A, B, C, and D.

TABLE 7

| Compound Tested | Human Lung Cancer Epithelial A549 micrograms/ml | Human Cervical Cancer Epithelial ME180 micrograms/ml | Human Breast Cancer Epithelial BT-20 micrograms/ml | Human Primary Mammary Epithelial HMEC micrograms/ml |
|---|---|---|---|---|
| Chloramphenicol | >40 | >40 | — | — |
| Erythromycin | >40 | >40 | — | — |
| Munumbicin A | 1 | 0.51 | 0.19 | 0.331 |
| Munumbicin B | 0.019 | 0.140 | 0.019 | 0.011 |
| Munumbicin C | 0.3 | 0.1 | 0.013 | 0.0023 |
| Munumbicin D | 2.6 | 0.2 | 0.07 | 0.425 |

TABLE 8

| Munumbicin | Yield per liter in mg | M.W. mass units | Molar∈ | Retention time in min. Dynamax col. | Retention time in min. Microsorb col. |
|---|---|---|---|---|---|
| A | 10 | 1326.5 | $218\lambda = 23,300$<br>$240\lambda = 424$ | 126.5 | 69.9 |
| B | 118 | 1269.6 | $208\lambda = 13,360$<br>$240\lambda = 54,514$<br>$420\lambda = 21,200$<br>$440\lambda = 22,065$ | 116.3 | 68.5 |
| C | 30 | 1298.5 | $220\lambda = 5,929$<br>$240\lambda = 62,072$<br>$416\lambda = 55,356$<br>$440\lambda = 56,785$ | 98.0 | 67.8 |
| D | 15 | 1312.5 | $221\lambda = 8,442$<br>$314\lambda = 220$<br>$404\lambda = 128$ | 80.8 | 45.0 |

Other smaller peaks with retention times of 45-75 minutes, that were bioactive, were also observed (FIG. 4). Components in each of these peaks, when assayed on PDA plates, challenged with *Pythium ultimum*, caused complete inhibition of fungal growth. This organism was chosen, among all others, because of its rapid growth characteristics and its sensitivity to anticancer compounds such as taxol (Young et al., 1992). Repassage of the contents of each peak over the same column gave compounds that were at least 95% homogeneous, as based on numbers of peaks and peak intensity, and were bioactive against *Pythium ultimum* and, thus, used for bioassay and other tests. Final and total purification of each component was obtained after passage through a Microsorb 100-5 C-18 column, 250×4.6 mm. The initial elution solvent was 20% acetonitrile: 80% water for 90 minutes programmed to a final concentration of 80% acetonitrile column ultimately yielding single peaks that have been designated munumbicins A, B, C, and D. Some indication of the purity of these compounds was also obtained by an NMR-COSY ($^1$H-$^1$H coupling) experiment in which each of the peaks, especially the smaller downfield ones, were coupled to the more intense upfield ones suggesting that the small peaks in the spectrum are not attributable to contaminating substances.

Each of the munumbicins reacted with ninhydrin to produce a weakly pinkish product on silica gel plates. This suggested that the compounds contained primary or secondary amino groups. Additionally, the absorption of each of these compounds in the region of 208 nm suggested the presence of one or more amido chromophoric groups (Table 8) (Silverstein et al., 1991).

Table 9 shows the amino acid composition of the munumbicins A, B, C, and D.

The results in Table 9 are presented as the averages of 3 individual amino acid analyses. Data are presented as mole percents with standard deviations of the mean. The number in parenthesis following each amino acid indicates the tentative number of moles of that residue per mole of the munumbicin. Hydrolysis of glutamine or asparagine resulted in deamination, therefore producing glutamic acid or aspartic acid, respectively. Therefore, it was possible only to determine the sums of each acid/amide combination which are referred to as Glx and Asx.

The molar ratios of the amino acids Glx, Pro, Thr, and Val were 1:2:1:3, respectively. Munumbicin C has an extra proline. Munumbicins A, B, and D contained 1 mole of Asx (aspartic acid or asparagine) (Table 9). A unique feature of munumbicin A was the presence of two moles of leucine (Table 9). The deduced molar ratios of amino acids were consistent with the observed molecular weights of the compounds.

Mass Spectroscopic Analyses

A mass spectrum was obtained for each of the HPLC purified munumbicins. Spectral data were obtained on a Bruker Biflex III MALDI mass spectrometer. The instrument was set on the reflective mode with an accelerating voltage of 19 KEV. A nitrogen laser at 337 nm at 3 Hz was used (having a 3 nanosecond pulse width). The number of spectra obtained on any individual sample varied from 10 to 200 shots. The matrix used for crystallization with the munumbicins was alpha-cyano-4-hydroxy cinnamic acid. External calibration to standardize the molecular weights was done with adrenocorticotropic hormone fragment 18-39=M.W. 2465.2. Data reported were presumed accurate to the first decimal place. In order to ascertain if any of the peaks in the mass spectra of the munumbicins was sodiated,

TABLE 9

| Amino Acid | Munumbicin A 1326.5 M.W. Mole Percent | | Munumbicin B 1269.6 M.W. Mole Percent | | Munumbicin C 1298.5 M.W. Mole Percent | | Munumbicin D 1312.5 M.W. Mole Percent | |
|---|---|---|---|---|---|---|---|---|
| Asx | 12.9 ± 1.4 | (1) | 14.1 ± 1.5 | (1) | 2.1 ± 0 | (0) | 10.0 ± 0.2 | (1) |
| Glx | 5.2 ± 2.3 | (1) | 9.0 ± 0.2 | (1) | 7.0 ± 0.1 | (1) | 8.6 ± 0.3 | (1) |
| Leucine | 20.1 ± 0.7 | (2) | 0 | (0) | 0 | (0) | 0 | (0) |
| Proline | 17.6 ± 1.1 | (2) | 21.3 ± 0.4 | (2) | 37.6 ± 0.7 | (3) | 22.9 ± 0.2 | (2) |
| Threonine | 7.3 ± 0.5 | (1) | 12.7 ± 0.3 | (1) | 11.3 ± 0.7 | (1) | 14.2 ± 0.3 | (1) |
| Valine | 32.1 ± 0.7 | (3) | 41.7 ± 0.7 | (3) | 40.9 ± 0.2 | (3) | 42.9 ± 0.3 | (3) |

*mole percent per residue is approximately 10.

Na$^+$ was added in excess to the sample prior to crystallization of the matrix and a spectrum was retaken.

Mass spectroscopy of each of the munumbicins revealed a range of actual masses from 1326.5 of munumbicin A, to that of 1298.6 representing munumbicin B (Table 8). Each of these masses represented the actual mass and not M+Na$^+$ since the addition of sodium ions to the sample used in the mass spectrometer, on any of the munumbicins, did not give an M+23 peak. Munumbicins recovered from the second passage through the Microsorb 60-8 Dynamax C-18 column, 250×10 mm (5 micron), were quite homogeneous as measured by HPLC. However, after mass spectroscopy, munumbicin A still had a small amount of a compound with a mass of 1266.2 associated with it, whereas munumbicin C had an associated component at 1314.5 in small quantities. Finally, munumbicin D had a series of components in much lesser amounts at 1328.5, 1314.5, and 1346. These components probably represent derivatives of the major components of the munumbicin series A-D. The phenomenon of a number of peptide derivatives of an antibiotic appearing in a culture broth is not uncommon in nature especially with the lipopeptides (Ballio et al., 1994).

NMR Spectroscopy

NMR spectroscopy was applied to each of the munumbicins with the greatest effort given to munumbicin B because of its availability relative to the other munumbicins. Samples were dissolved in 100% deuterated acetonitrile and data obtained in a Bruker 500 MHz instrument. In $^1$H spectroscopy, each sample was subjected to 16 scans with a sweep width of 6024 and 8 k real points. A gradient enhanced COSY ($^1$H-$^1$H coupling) experiment was also conducted with munumbicin B.

Figure 5:
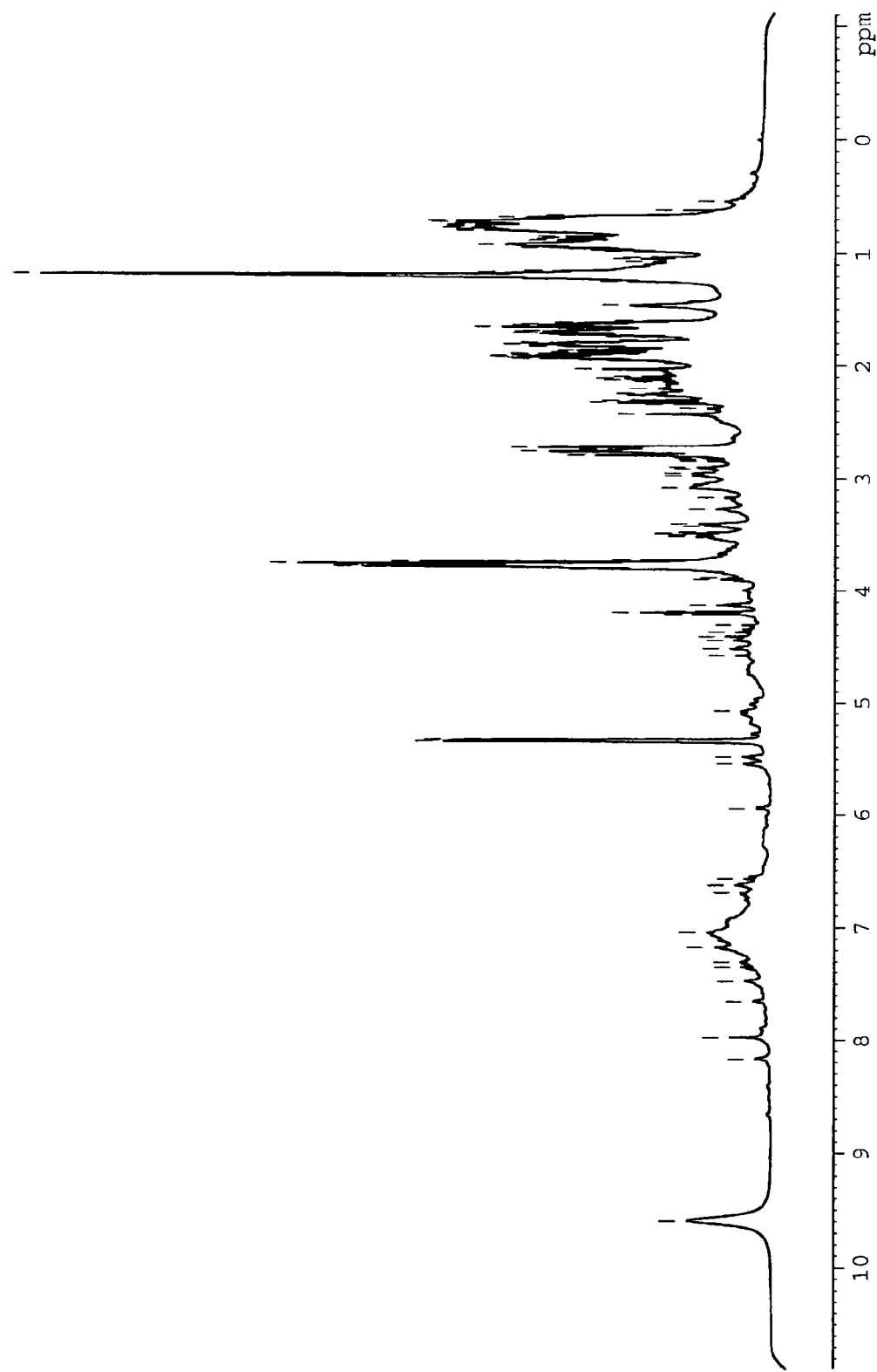
FIG. 5 shows the $^1$H NMR spectrum of munumbicin B (CDCl$_3$, 500 MHz).

The $^1$H NMR of the munumbicins (e.g., munumbicin B) was compatible with the peptide nature of the molecules. However, absorbances at 5.5-6.0 ppm suggested C—C unsaturation which is not found in the peptide moiety of the molecule (Strobel et al., 1999) (FIG. 5). In addition, the absorbances between 3.5-5.0 ppm were suggestive of the presence of a sugar moiety. Therefore, each of the munumbicins was analyzed for sugar residues after acid hydrolysis, reduction, acetylation, and GC-mass spectrometry. There was not a trace of sugars in any of the munumbicin preparations. Thus, the absorption peaks in this portion of the $^1$H NMR spectrum were not those of sugar residue protons, but protons associated with carbons bearing oxygen or nitrogen (Silverstein et al., 1991). The $^1$H NMR spectrum of each of the other munumbicins was related but not identical to munumbicin B (FIG. 6).

The $^1$H NMR spectrum of a munumbicin B comprises $^1$H chemical shifts shown in FIG. 5.

The $^1$H NMR spectrum of a munumbicin C comprises $^1$H chemical shifts shown in FIG. 7.

The $^1$H NMR spectrum of a munumbicin D comprises $^1$H chemical shifts shown in FIG. 9.

The relative intensity of absorption peaks in munumbicin B from 0.5-2 ppm was consistent with an abundance of methyls and methylenes in the molecule. The unsaturated nature of these molecules was also consistent with the strong UV absorbances seen in the UV spectra of the molecules especially munumbicins B and C (Table 8). These absorbances were contributed by the non-peptide portion of the munumbicins since there was no amino acid present in any of the munumbicins that absorbed in the UV above 230 λ (Table 8). Furthermore, the highly colored nature of each of the munumbicins (yellowish-orange-reddish) suggested that the non-peptide portion of the molecule was the contributing pigment. However, coloration may be due to a metal complex with the peptide portion of the molecule.

The $^{13}$C NMR spectrum for purified munumbicin A comprises $^{13}$C chemical shifts of shown in FIG. 6. The $^{13}$C NMR spectrum for purified munumbicin B comprises $^{13}$C chemical shifts shown in FIG. 6. The $^{13}$C NMR spectrum for purified munumbicin C comprises $^{13}$C chemical shifts shown in FIG. 8. The $^{13}$C NMR spectrum for purified munumbicin D comprises $^{13}$C chemical shifts shown in FIG. 10.

Modifications in the amino acid composition of these compounds allowed for some of the molecular weight variation that was observed in them (Table 8). Likewise, it was apparent that modifications also occurred in the non-peptide portion of the munumbicins, given the slight variation in masses of the minor components that have been noted, e.g., munumbicin D–MW=1312.5, with a minor component at 1314.5 suggesting the difference of one double bond in the molecule. Overall, the peptide portion of these compounds generally contributed about 70-80% of the mass of each munumbicin and knowledge about the non-peptide moieties of these substances was still lacking. Based on the known molecular weights of the components it appeared that the non-peptide component must be in the range of 300-400 mass units and the limited spectroscopic data available suggested that it may be a macrolide.

Overall, it appeared that the munumbicins represent a novel group of bioactive substances since a comprehensive search of the *Chapman & Hall Dictionary of Natural Products on CD ROM,* 2001, did not reveal complete chemical identity with any previously described products, although some similarity in products with comparable masses are known in the literature. Among these is the arbocandin E (Chapman & Hall Number JOX 54-Q-S) with a MW of 1298.5 which is identical to munumbicin C (Table 8). Another is arbocandin F (Chapman & Hall number JOX 55-R) having a MW of 1312.5 which is identical to munumbicin D (Table 8). However, the arbocandins originating from a filamentous fungus, are glucan synthase inhibitors, and contain certain amino acid residues in quantity and quality not found in the munumbicins and these inhibitors are not pigmented.

Example 11

Isolation of Other Biologically Active Endophytic Streptomycetes

The procedure for selecting endophytic *Streptomyces* spp. described in Examples 1 and 2 was applied to other plants carefully selected from certain environmental settings. Plates were continuously monitored for spore formation by stereo and light microscopy. In some cases, individual Streptomycete colonies were obtained only after 2-3 weeks or even longer, because of their small size. They also tended to have close proximity to the plant material and care was needed to obtain them in a pure culture. In other cases they were located beneath the plant material that was placed on the water agar plate. Because of the extended incubation time and their small size these colonies were easily overlooked and may not have been observed by previous workers.

Using the methodology described in Examples 1 and 2, it was possible to acquire a number of other *Streptomyces* spp. Each of these species was shown by microscopic techniques to be a streptomycete primarily based on small spore size and the occurrence of spores in chains. In addition each of these has been cultured as described above and shown via bioassay techniques to have antifungal and antibacterial activities. These streptomycetes have been acquired from higher plants around the world and have potential as a biological source of novel useful products. Other representative biologically active *Streptomyces* spp. obtained from higher plants as endophytes by these methods are provided in Table 10.

TABLE 10

| Plant Source | Lab Code | Lab number | GPS location | Biological Activity* |
|---|---|---|---|---|
| *Chiliotrichum difusum* | C-6 | 18 | 50° 54' 11" S 72° 43' 53" W | Pythium ++ |
| *Nothofagus betuloides* | C-9 | 25 | 51° 06' 03" S 72° 58' 56" W | Pythium ++ |
| *Chiliotrichum difusum* | C-6 | 41 | 50° 54' 11" S 72° 43' 53" W | Pythium + |
| *Chiliotrichum difusum* | C-6 | 20 | 50° 54' 11" S 72° 43' 53" W | Pythium + |
| *Desfontainia Spinosa* | C-17 | 33 | 41° 32' 42" S 72° 36' 14" W | Pythium + |
| *Nothofagus pumilio* | C-3 | 64 | 50° 55' 18" S 72° 42' 41" W | Pythium + |
| *Nothofagus Antartica* | C-7 | 62 | 50° 52' 30" S 72° 44' 13" W | Pythium + |
| *Drymis winteri* | C-14 | 36 | 41° 32' 42" S 72° 36' 14" W | Pythium + |
| *Nothofagus betuloides* | C-99 | 27 | 51° 06' 03" S 72° 58' 56" W | Pythium ++ |
| *Podocarpus nubigena* | C-12 | 19 | 41° 32' 52" S 72° 35' 39" W | Pythium + |
| *Misodendrum punctulatum* | C-1 | 38 | 50° 58' 25" S 72° 52' 27" W | Pythium + |
| *Ceiba pentandra* | Ti-2 | — | 12° 21' 08" S 70° 42' 32" W | Pythium + |
| *Grevellia Pteridifolia* | A35-1 | — | 12° 59' 39" S 132° 28' 50" E | Pythium ++ |
| *Dunalia purpurea* | P2-24 | — | No readings | Pythium + |

The "+" sign indicates relative activity against *Pythium ultimum* in the bioassay test. Generally, activity against this fungus is an excellent indication that the organism and its extracts will possess anticancer activity.

These biologically active endophytic Streptomycetes were deposited in the Montana State University culture collection according to the numbers assigned to them above. In addition, other isolates from unidentified vines in the Lake Sandoval region of Peru have been isolated and were designated as Peru P-591, P-25 and P01-24.

Example 12

Isolation and Identification of the Endophytes of *Grevellia pteridifolia*

Stems (0.5-1.0 cm in diameter) of *Grevellia pteridifolia* were obtained from Kakadu National Park of the Northern Territory, Australia at 12° 59' 39" South and 132° 28' 50" East. The stems were thoroughly treated with 70% ethanol and then the outer bark removed with a sterilized sharp blade. The inner pieces of the stem, containing the cambium, phloem and xylem tissues, were plated on water agar in Petri plates. After incubation for at least 7-10 days (sometimes longer) at 23° C., individual fungal and bacterial colonies were removed with a sterile fine tipped needle and transferred onto potato dextrose agar (PDA).

The stems of Grevellia pteridifolia yielded numerous endophytic microorganisms, some of which were *Pestalotiopsis* spp., which is common for plants growing in tropical or semi-tropical environments (Li et al., 2001). One endophyte, designated A35-1 (NRRL 30566), showed strong antimicrobial activity. This organism resembled a *Streptomyces* sp. and was not isolated as an endophyte from any plants in the near vicinity of the fern-leafed *Grevellia*.

The putative streptomycete was grown on gamma-irradiated carnation leaves and was studied for its ability to make spores which it did profusely.

The organism fits, in all respects, the definition of a *Streptomyces* sp. It produced slow growing, whitish-grey colonies having a whitish felt-like appearance on PDA. However it flourished on Nutrient agar and produced colonies with a comparable description to those on PDA.

Fruiting structures of the microorganism appearing on both carnation leaves and the tissues of the host plant were examined by stereo and light microscopy. These structures were fixed and processed using the standard methods of fixation (Worapong et al., 2001) by placement in 2% (v/v) glutaraldehyde in 0.1 M sodium cacodylate buffer (pH 7.2) and left overnight. The samples were then passed through a gradient of ethanol solutions to discourage the processes of shriveling which normally occurs in spores and mycelia with rapid dehydration. The samples were then critical-point dried, gold coated with a sputter coater, and observed and photographed with a JEOL 6100 scanning electron microscope.

Figure 11:
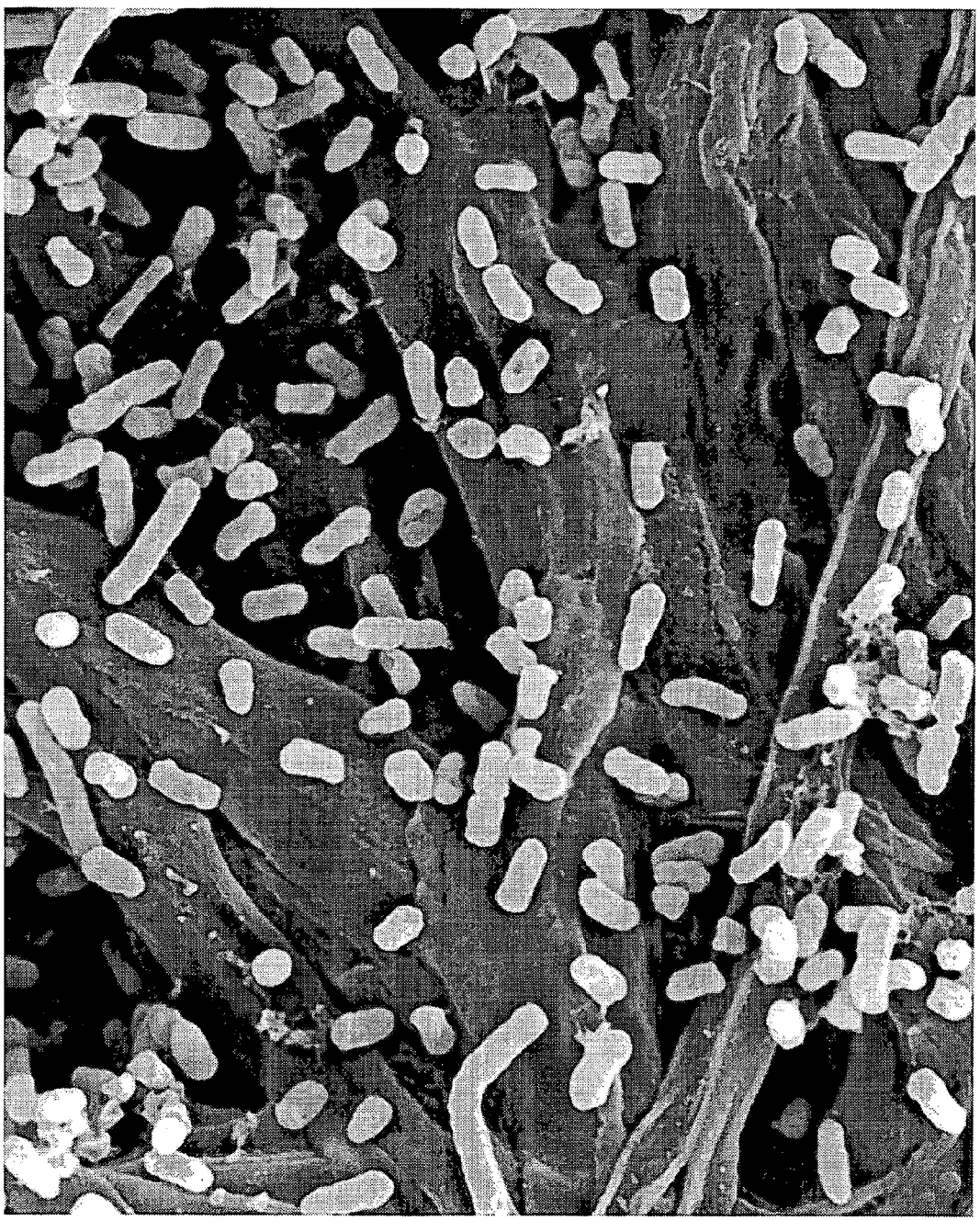
FIG. 11 shows a scanning electron micrograph of the mycelium and spores of Streptomyces NRRL 30566, the source of kakadumycin. The photo is magnified 17,000 times.

An examination of the organism by scanning electron microscopy revealed the presence of numerous aerial filaments, and generally smooth cylindrical spores, (about 0.5-0.6 micron in diameter×0.8-1.3 microns in length) (FIG. 11).

Example 13

Isolation Procedures for the Kakadumycins

Small blocks of PDA containing *Streptomycete* sp. A35-1 (NRRL 30566) were inoculated into 500 ml of nutrient broth in a 2 liter Erlenmeyer flask and incubated at 27° C. with shaking for 4-6 days. The culture filtrate was then extracted three times with ½ volumes of methylene chloride. The extracts were pooled and then taken to dryness under flash evaporation at 40° C. The yield of dry material per liter was about 40 mg per liter. Then, the dried material was dissolved in a small volume of chloroform and placed on a 2.5×9 cm silica gel column, rinsed with 200 ml of chloroform, and then eluted with 100 ml of chloroform:methanol 50:1 v/v. the active compound eluted with as a yellowish band. The eluate was flash evaporated and then approximately 5 mg of the material was subjected to high pressure liquid chromatography (HPLC) on a Microsorb 60-8 Dynamax C-18 column, 250×10 mm (5 micron). The elution solvent was 20% acetonitrile:80% water programmed for 90 minutes to a final concentration of 65% acetonitrile:35% water. The elution stream was continuously monitored at 260 nm at a flow rate of 2 ml/minute.

Individual fractions were subjected to a bioassay test by placing them on a Petri plate with PDA, drying, and then challenging with small blocks of agar containing *Pythium ultimum*. The fractions were considered active if inhibition of fungal growth was observed. Each fraction was repurified using the same HPLC system and the fractions were weighed and primarily used for bioassay tests. The compounds in the fractions were at least 95% pure. Final purification for spectroscopic measurements was made by subjecting the compound(s) of interest to HPLC by passage over a Symmetry C-18 column, 150×4.6 mm (3.5 micron), using acetonitrile and water at the concentrations and pro-grams as given above. The elution times of the compounds designated kakadumycins A, B, and C were 73, 77.5 and 107 minutes, respectively.

Example 14

Kakadumycin A Extracts from *Streptomyces* sp. A3-5-1 Against Human Pathogens

Kakadumycin A was evaluated in the general disk screening test described in Example 4 involving human pathogenic bacteria and yeast. The diameter of the zone of inhibition was taken as a relative indication of biological activity of kakadumycin. Most notable from this testing regimen was that most of the Gram positive bacteria tested were sensitive to the kakadumycin extracts and some Gram negative bacteria as well such as *E. coli*. Table 11 shows the inhibitory activity of kakadumycin A and some standard antibiotics against various bacteria (standard growth conditions) in a disk diffusion assay conducted on Muller Hinton broth agar medium at 35° C., unless otherwise noted. Kakadumycin A was also inhibitory to a number of human pathogenic fungi (Table 11).

TABLE 11

| Gram | Organism | ATCC # | Disk Diffusion with Chloramphenicol (30 micrograms) | Disk Diffusion with A3-5-1 (10 micrograms) | Test Media and conditions |
|---|---|---|---|---|---|
| | BACTERIA | | | | |
| − | *Acinetobacter spp.* | 49137 | 8 mm | 19 mm | MHA −35° C. |
| − | *Burkholderia cepacia* | 25416 | not tested | 7 mm | MHA −35° C. |
| − | *Eschericia coli* | 10536 | 28 mm | 12 mm | MHA −35° C. |
| − | *Eschericia coli* | 25922 | 29 mm | 7 mm | MHA −35° C. |
| − | *Eschericia coli* | 35218 | R | 11 mm | MHA −35° C. |
| − | *Haemophilus influenzae* | 49247 | 23 mm | 10 mm | HTM 35° C. with 5% CO2 |
| − | *Haemophilus influenzae* | 49766 | not tested | 15 mm | HTM 35° C. with 5% CO2 |
| − | *Klebsiella pneumoniae* | 10031 | Cip (5 micro-)-34 grams mm | R | MHA −35° C. |
| − | *Neiseseria gonorrhoeae* | 49266 | 33 mm | 27 mm | GCA w/ 1% supplement in 5% CO2 |
| − | *Pseudomonas aeruginosa* | 27853 | R | R | MHA −35° C. |
| − | *Salmonella typhimurium* | 13311 | 28 mm | R | MHA −35° C. |
| − | *Shigella dysenteriae* | 11835 | 40 mm | 11 mm | MHA −35° C. |
| − | *Stenotrophomas maltophilia* | 13637 | 28 mm | 16 mm | MHA −35° C. |
| + | *Enterococcus faecalis* | 29212 | 20 mm | 20 mm | MHA −35° C. |
| + | *Enterococcus faecalis* (VRE) | 51299 | 8 mm | 15 mm | MHA −35° C. |
| + | *Enterococcus faecium* | 49624 | 25 mm | 22 mm | MHA −35° C. |
| + | *Enterococcus faecium* | 51559 | not tested | 25 mm | MHA −35° C. |
| + | *Micrococcus luteus* | 9341 | not tested | 28 mm | MHA −35° C. |
| + | *Staphylococcus aureus* (MRSA) | 33591 | Cip (5 micro-)-26 grams mm | 20 mm | MHA −35° C. |
| + | *Staphylococcus aureus* | 29213 | 25 mm | 18 mm | MHA −35° C. |
| + | *Staphylococcus aureus* | 29737 | not tested | 19 mm | MHA −35° C. |
| + | *Staphylococcus aureus* (GISA) | 700699 | 26 mm | 23 mm | MHA −35° C. |
| + | *Staphylococus aureus* (GISA) | 700787 | 29 mm | 20 mm | MHA −35° C. |
| + | *Staphylococcus epidermidis* | 12228 | 30 mm | 25 mm | MHA −35° C. |
| + | *Streptococcus pneumoniae* | 49619 | 22 mm | 19 mm | MHA w/5% dsb 35° C. w/5% CO2 |
| | YEASTS/FUNGI | | Flucytosine (10 micrograms) | | |
| | *Candida albicans* | 24433 | 20 mm | R | RPMI-glucose agar −35° C. |
| | *Candida albicans* | 90028 | 37 mm | R | RPMI-glucose agar −35° C. |
| | *Candida glabrata* | 2001 | 53 mm | 29 mm | RPMI-glucose agar −35° C. |
| | *Candida krusei* | 6258 | 7 mm | R | RPMI-glucose agar −35° C. |
| | *Candida parapsilosis* | 22019 | 46 mm | R | RPMI-glucose agar −35° C. |
| | *Candida parapsilosis* | 90018 | 57 mm | R | RPMI-glucose agar −35° C. |
| | *Candida tropicalis* | 750 | 47 mm | 7 mm | RPMI-glucose agar −35° C. |
| | *Cryptococcus neoformans* | 32045 | 42 mm | 21 mm | RPMI-glucose agar −35° C. |
| | *Saccharomyces cerevisiae* | 9763 | 50 mm | R | RPMI-glucose agar −35° C. |

Example 15

Anticancer Cell Line Tests

Kakadumycin A was tested against three human cancer cell lines (ATCC) and human primary mammary epithelial cells using the procedure described above for the munumbicins. Kadadumycin B was tested against one human cancer cell line. Echinomycin was also run for comparison.

Human red blood cells were not affected up to 80 micrograms/ml, by kakadumycin A or kadadumycin B, but other human tissues show adverse effects of kakadumycin A and kadadumycin B as shown in Table 12.

Tests against a primary human cell line, human mammary epithelial cells, (Clonetics, Walkersville, Md.), showed that both kakadumycin A and kakadumycin B displayed cytotoxicity with $IC_{50}$'s of 9.0±1.4 and 10.5±1.4 nanograms/ml, respectively. Echinomycin displayed cytotoxicity with an $IC_{50}$ of 10.8±1.1. Furthermore, both kakadumycin A and kakadumycin B were active against the human breast cancer cell line BT 20 with $IC_{50}$'s of 8.0 and 8.0 ng/ml, respectively. Echinomycin was active against the human breast cancer cell line BT 20 with an $IC_{50}$ of 4.8 standards. Other details of these analyses, as performed on a peptide antibiotic from another endophytic organism, have been described (Miller et al., 1998; Castillo et al, 2002). Each analysis was performed at least three times and the averages presented along with the standard deviation of the mean.

HPLC preparations (from a Symmetry C-18 column, 150×4.6 mm (3.5 micron), Example 13) of the kakadumycins were used to chemically characterize this compound. Authentic echinomycin (Sigma Chem Co., St. Louis, Mo.) was used for comparison. The major component of the culture medium of *Streptomyces* sp. A35-1 (NRRL 30566) appeared as a peak with a retention time of 73.0 minutes on the Symmetry C-18 column. This HPLC technique was used to prepared amounts of the compound eventually used for bioassay and analytical purposes.

The resulting compound, designated kakadumycin A, reacted with ninhydrin to produce a weakly yellowish to brownish product on silica gel plates indicating that the compound contained secondary amino groups. Additionally, the UV absorption of kakadumycin in the region of 205 nm suggested the presence of one or more amido chromophoric groups (Silverstein et al., 1991). In addition, the peaks at 238

TABLE 12

| Compound Tested | Human Lung Cancer Epithelial A549 micrograms/ml | Human Cervical Cancer Epthelial ME180 micrograms/ml | Human Breast Cancer Eipthelial BT-20 micrograms/ml | Human Primary Mammary Epithelial HMEC micrograms/ml |
|---|---|---|---|---|
| Kakadumycin A | 0.270 | 0.024 | 0.008 | 0.009 |
| Kakadumycin B | | | 0.008 | 0.0105 |
| Echinomycin | 0.145 | 0.023 | 0.0048 | 0.0108 |

Example 16

Chemical Characterization of Kakadumycins

Amino Acid Analysis

HPLC purified kakadumycins were dissolved in 50% (v/v) methanol in water, placed in 6×50 mm glass tubes, dried in vacuo, and then transferred to a hydrolysis vessel (PN007603, Millipore, Marlborough, Mass., USA; part no. 007603). Approximately 300 microliters of 6 N HCl were added to the vessel which was then alternatively purged with nitrogen and evacuated three times before being sealed under vacuum. Vapor phase hydrolysis was performed by heating at 110° C. for 22 hours. After cooling, the hydrolysis tubes were removed from the reaction vessel and dried in a centrifugal concentrator (SpeedVac, ThermoSavant, Holbrook, N.Y.) for 30 minutes. Samples were then derivatized and analyzed by two different methods, ion-exchange chromatography followed by post-column ninhydrin detection and pre-column 6-aminoquinolyl-N-hydroxysuccinimidyl carbamate (AQC) derivatization followed by reverse phase HPLC. In the former case, the analysis was purified on a Beckman Model 6300 Amino Acid Analyzer. In the latter case, an Alliance/Millenium HPLC system (Waters, Milford, Mass.) equipped with an AccQTag amino acid analysis column was used. The ninhydrin and AQC chemistries were performed according to the manufacturer's instructions. Separation and quantitation of amino acids was carried out on a Beckman Model 6300 Amino Acid Analyzer. Moles of each amino acid were initially determined using molar absorption extinction coefficients derived from amino acid nm and 315 nm were probably due to chemical bonding occurring in the molecule at positions not associated with the peptide moiety.

Amino acid analysis of kakadumycin A revealed the presence of serine:alanine:unknown amino acid at a ratio of 1:2:"estimated" 3.

Repeated amino acid analysis of kakadumycin A and echinomycin yielded comparable molar ratios of serine to alanine of (1:2 mole:mole) and revealed a substantial amount of an unknown, amino-containing compound, which eluted after ammonia when analyzed by ion-exchange chromatography and after proline when analyzed using reverse phase chromatography. The unknown did not co-elute with either methyl-N—N-methyl-valine or methyl-alpha-methyl-valine, the former of which is reported as a major constituent residue of echinomycin (Waring and Wakelin, 1974) and which may degrade upon acid hydrolysis. The presence of only 1 mole of serine rather than the expected two moles is probably related to the fact that serine is somewhat unstable upon conditions of acid hydrolysis (Waring and Wakelin, 1974).

A secondary kakadumycin compound of the *Streptomyces* sp. A35-1 strain, designated kakadumycin B, was also characterized. Kakadumycin B appeared as a peak with a retention time of 77.5 minutes on a Symmetry C-18 column, 150×4.6 mm (3.5 micron). This HPLC technique was used to prepared amounts of the compound eventually used for bioassay and analytical purposes.

The resulting compound, designated kakadumycin B, had UV absorption peaks at 239, 316, and 272 nm and a retention time of 77.5 minutes on a Symmetry C-18 column, 150×4.6 mm (3.5 micron). Amino acid analyses revealed a molar ratio of serine to alanine of 1:2. The unknown amino acid found in kakadumycin A was not present in kakadumycin B.

A third kakadumycin, kakadumycin C, was also characterized as having UV absorption bands at 204, 221, 246 and 307 nm. This compound had a retention time of 107 minutes on a Symmetry C-18 column, 150×4.6 mm (3.5 micron).

Mass Spectroscopic Analyses

A mass spectrum was obtained for each of the HPLC purified kakadumycins and echinomycin (authentic standard) using a Bruker Biflex-III MALDI/TOF mass spectrometer. The instrument was operated in the reflectronmode with an accelerating voltage of 19 KeV. A nitrogen laser (337 nm), with a pulse width of 3 nanoseconds and pulse frequency of 3 Hz was used for desorption and ionization of the Cursory examination of the MALDI mass spectrum of sodiated kakadumycin A (MW 1123.42) appeared as though it had molecular identity to sodiated echinomycin (*Chapman and Hall, Dictionary of Natural Products on CD ROM*, 2002). Also, MALDI analysis commonly showed an M+39 ($K^+$) peak in both echinomycin and kakadumycin A indicating a MW of 1100 of the parent compound. However, HR-MALDI yielded accurate masses of both echinomycin and kakadumycin and they were different (Table 13). A high probability empirical formula of each compound showed differences in the elemental composition of the two compounds (Table 13). For instance, kakadumycin A possessed 1 additional carbon atom, 2 additional protons, and 1 less nitrogen than echinomycin and this would predict that other physical and chemical characteristics would be different (Table 13).

TABLE 13

Chemical and chromatographic similarities and differences between echinomycin and kakadumycin A

| Characteristic Examined | Kakadumycin A | Echinomycin (Standard) |
|---|---|---|
| MALDI- HR mass spec. | 1123.4192 (sodiated) | 1123.4106 (sodiated) |
| Best fit empirical formula | $C_{52}H_{66}N_{11}O_{12}S_2Na$ | $C_{51}H_{64}N_{12}O_{12}S_2Na$ |
| HPLC- MS/M S; Main fragment ions of mass 1101 (H+) | MS/MS of fragment ions* Major ion 420: 147.6, 185.3, 291, 318.9, 346.1, 376.1, 390.1 Major ion 847.2: 277.9, 390.1, 420, 533.1, 724.9 | MS/MS of fragment ions* Major ion 420: 189.1, 260.3 287.9, 319.1, 346, 369, 376, 390 Major ion 847.2: 276.6, 420.1, 533.1, 538.4, 705.2 |
| Solubility in acetonitrile | soluble | sparingly soluble |
| Retention HPLC (system A) min. | 70.83 | 87.23 |
| Retention HPLC (system B) min. | 64.22 | 71.02 |
| $R_F$ ... TLC (system W) | 0.60 | 0.60 |
| $R_F$ TLC (system X) | 0.26 | 0.21 |
| $R_F$ TLC (system Y) | 0.40 | 0.34 |
| $R_F$ TLC (system Z) | 0.27 | 0.16 |
| UV absoptivity (nm) and millimolar extinction coefficients | 205 nm, $\epsilon$ = 7.48; 238 nm, $\epsilon$ = 7.22; 312 nm, $\epsilon$ = 5.28 | 205 nm, $\epsilon$ = 7.48; 238 nm, $\epsilon$ = 7.22; 312 nm, $\epsilon$ = 6.60 |

*The intensities of the fragment ions reported here are at least 20% of the total intensity of all ions observed in any given analysis.

sample. The number of spectra obtained on any individual sample varied from 10 to 200 laser shots. The matrix used for co-crystallization of the samples was alpha-cyano-4-hydroxy cinnamic acid. External calibration for the initial determination of the molecular weights was done with a mixture of peptides using their mono-isotopic protonated masses: bradykinin (M+H=1060.5690), angiotensin I (M+H=1296.6853), and somatstatin (M+H=1637.7244), and, in some cases, adrenocorticotropic hormone fragment 18-39=M.W. 2465.2. Data reported were presumed accurate to the first decimal place. In order to ascertain if any of the peaks in the mass spectra of the kakadumycin A was sodiated, $Na^+$ was added in excess to the sample prior to crystallization of the matrix and a spectrum was retaken. High resolution mass spectroscopy was performed on a Bruker Biflex-III mass spectrometer with the standard peptide mixture co-crystallized with the sample. LC/MS data were acquired on both kakadumycin A and echinomycin on a Bruker Esquire 3000 system with the sample in acetonitrile having a flow rate of 5 microliters/minute The counter current drying gas was at 250° C. having a flow rate of 4.0 l/minute.

Mass spectroscopy of kakadumycin A revealed a major peak at 1100.41 daltons. Kakadumycin B had a mass of 1053.3 daltons while kakadumycin C had a mass of 1068.4 daltons.

NMR Spectroscopy

Figure 12:
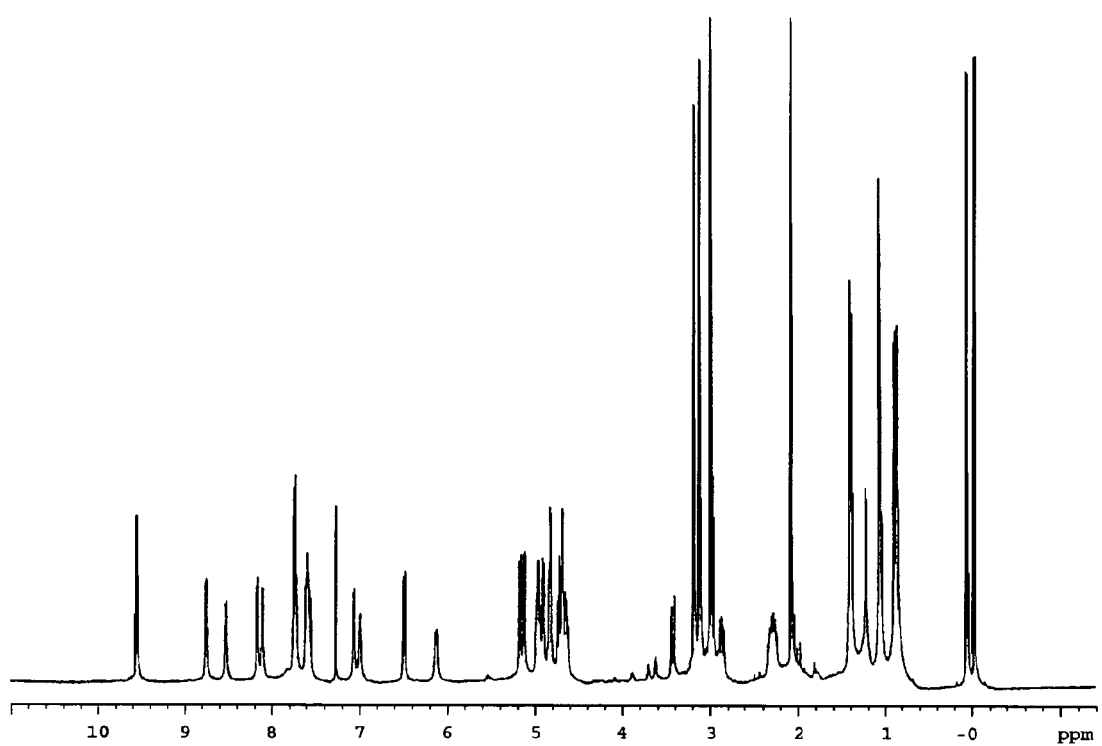
FIG. 12 shows the $^1$H NMR spectrum of kakadumycin A (CDCl$_3$, 500 MHz).

NMR spectroscopy was applied to kakadumycin A. Samples were dissolved in 100% deuterated chloroform and data obtained in a Varian 500 MHz instrument. In $^1$H NMR spectroscopy, each sample was subjected to 16 scans with a sweep width of 6024 and 8 k real points. The $^1$H NMR spectrum of kakadumycin A was compatible with the peptide nature of the molecules and demonstrated that the methods of kakadumycin A preparation yielded a pure product (Silverstein et al., 1991; Ballio et al., 1994) (FIG. 12). The $^1$H NMR spectrum was also uniquely characteristic for this particular molecule. The $^1$H NMR spectrum ($CDCl_3$, 500 MHz) of a kakadumycin A comprises $^1$H chemical shifts shown in FIG. 12.

The $^1$H NMR spectrum ($CDCl_3$, 500 MHz) of a kakadumycin B comprises $^1$H chemical shifts shown in FIG. 15.

The $^{13}$C NMR spectrum for purified kakadumycin A comprises $^{13}$C chemical shifts shown in FIGS. 13 and 14. The $^{13}$C NMR spectrum of kakadumycin A clearly showed the presence of a clean (no contaminating molecules) carbon spectrum (FIGS. 15 and 16). The carbon resonances showed the presence of methyl, methylene, and methine carbons (FIGS. 15 and 16).

The $^{13}$C NMR spectrum for purified kakadumycin B comprises $^{13}$C chemical shifts shown in FIG. 16.

Kakadumycin A has a molecular weight of 1100.41. A number of other known compounds also have a molecular weight in this size range including Bradykinin Potentiator C, Ferrirubin, and Mussaendoside M, according to a comprehensive search of the *Chapman & Hall Dictionary of Natural Products on CD ROM*, 2001. However, none of these compounds has a molecular weight that is identical to kakadumycin A. In addition, closer examination revealed that none of the previously described molecules had the amino acid composition of kakadumycin A, nor, in fact does kakadumycin A have the chromophoric, siderophoric properties or sugar content of the previously described substances. Thus, kakadumycin A is a novel bioactive product with chemical and biological properties. The same rationale applies to kakadumycins B and C.

Chromatographic Methods

Authentic echinomycin was compared to kakadumycin A by both HPLC and TLC methods. Two HPLC systems were employed and these include (System A) a Waters' Symmetry C-18 column, 150×4.6 mm (3.5 micron), programmed with an acetonitrile:water gradient at 20%/80% to a final concentration of 70%/30% after 120 minutes and (System B) using the same column as (A) having all conditions the same except for the addition of 0.01% v/v of trifluroacetic acid. For thin layer chromatography (TLC) four solvent systems were used on 0.25 mm (5×10 cm) Merck silica gel plates and after separation, the plates were viewed under short wave length UV light and the $R_F$'s recorded. The systems were (W) ethyl acetate:methanol 9:1 v/v, (X) methyl acetate:acetonitrile 9:1 v/v, and (Y) ethyl acetate:acetonitrile 7:3 v/v and (Z) n-butanol:acetic acid:water 3:1:1 v/v.

The retention times of the two compounds, in both HPLC systems used, were also noticeably different (Table 13). Mixing experiments in the HPLC systems with the two compounds yielded an asymmetric peak having a broad shoulder suggesting incomplete separation had occurred. For the most part, TLC systems that incorporated esters and acetonitrile produced the best mobility differences between the two substances (Table 13), while system W did not yield any separation whatsoever. Ultraviolet absorption peaks and molar absorption extinction coefficients for each compound were calculated and both showed the same absorption bands and extinction coefficient values at 205 and 238 nm, but the extinction coefficient values at 312 nm for the two compounds were different (Table 13).

Example 17

Other Kakadumycins

In the HPLC preparations of kakadumycin A from a Symmetry C-18 column, 150×4.6 mm (3.5 micron), a shoulder peak with a lower retention appeared on the main peak of kakadumycin A at 77.5 minutes. This peak yielded a MALDI mass spectrum consisting of a major peak at 1053.5, and smaller peaks at 1102.5 and 1123.5, which could be indicative of other compounds related to kakadumycin A. Further treatment of the preparation with sodium did not enhance the peak intensity suggesting that the 1053.5 component has a MW of 1030.5 and the molecule had picked up one $Na^+$. Traces of this compound designated kakadumycin B generally appeared in the kakadumycin A preparations. Also present in kakadumycin A preparations were traces of a compound whose mass was 1102.5 and a protonated 1101.5 could account for this ion. Likewise, this molecular species (1101.5) was consistent as a relative of the anhydro-alanine-1030 (kakadumycin B). Hypothetically, kakadumycin B (MW=1030.5) could lack one anhydro-alanine residue (mass 71), accounting for its presence and possible relatedness to the 1101 MW component. Furthermore, in commercial preparations of echinomycin, a 1053.5 ion was present. Comparative LC-MS-MS of this 1053 ion in echinomycin and kakadumycin A yielded different fragmentation patterns suggesting structural differences.

A general disk screening test was also applied to a series of human pathogenic bacteria with kakadumycin B. Table 14 shows the inhibitory activity of the kakadumycin B.

TABLE 14

| Gram | Organism | ATCC # | Disk Diffusion at (10 μg) | Disk Diffusion with Control antibiotic | Test Media and conditions |
|---|---|---|---|---|---|
| | BACTERIA | | | | |
| − | *Acinetobacter* spp. | 49137 | 11 mm | 26 mm (cipro) | MHA −35° C. |
| − | *Burkholderia cepacia* | 25416 | R | 24 mm (cipro) | MHA −35° C. |
| − | *Escherichia coli* | 10536 | | | MHA −35° C. |
| − | *Escherichia coli* | 25922 | 8 mm | 26 mm (chloram) | MHA −35° C. |
| − | *Escherichia coli* | 35218 | | | MHA −35° C. |
| − | *Haemophilus influenzae* | 49247 | | | HTM 35° C. with 5% $CO_2$ |
| − | *Haemophilus influenzae* | 49766 | | | HTM 35° C. with 5% $CO_2$ |
| − | *Klebsiella pneumoniae* | 10031 | R | 32 mm (cipro) | MHA −35° C. |
| − | *Neiseseria gonorrhoeae* | 49266 | | | GCA w/1% supplement in 5% $CO_2$ |
| − | *Pseudomonas aeruginosa* | 27853 | R | 30 mm (cipro) | MHA −35° C. |
| − | *Salmonella typhimurium* | 13311 | R | 28 mm (chloram) | MHA −35° C. |
| − | *Shigella dysenteriae* | 11835 | 10 mm | 24 mm (cipro) | MHA −35° C. |
| − | *Stenotrophomas maltophilia* | 13637 | 13 mm | 25 mm (chloram) | MHA −35° C. |
| + | *Enterococcus faecalis* | 29212 | 20 mm | 20 mm (chloram) | MHA −35° C. |
| + | *Enterococcus faccalis* (VRE) | 51299 | 21 mm | 23 mm (cipro) | MHA −35° C. |
| + | *Enterococcus faecium* | 49624 | 22 mm | 20 mm (chloram) | MHA −35° C. |
| + | *Enterococcus faecium* | 51559 | | | MHA −35° C. |

TABLE 14-continued

| Gram | Organism | ATCC # | Disk Diffusion at (10 μg) | Disk Diffusion with Control antibiotic | Test Media and conditions |
|---|---|---|---|---|---|
| + | Micrococcus luteus | 9341 | 28 mm | 29 mm (chloram) | MHA –35° C. |
| + | Staphylococcus aureus (MRSA) | 33591 | 22 mm | 27 mm (cipro) | MHA –35° C. |
| + | Staphylococcus aureus | 29213 | 17 mm | 19 mm (chloram) | MHA –35° C. |
| + | Staphylococcus aureus | 29737 | | | MHA –35° C. |
| + | Staphylococcus aureus (GISA) | 700699 | 22 mm | 29 mm (chloram) | MHA –35° C. |
| + | Staphylococcus aureus (GISA) | 700787 | | | MHA –35° C. |
| + | Staphylococcus epidermidis | 12228 | 23 mm | 31 mm (chloram) | MHA –35° C. |
| + | Streptococcus pneumoniae | 49619 | 22 mm | 24 mm (cipro) | MHA w/5% dsb –35° C. w/5% $CO_2$ |

Example 18

Comparative Biological Activities

Microbroth dilution assays of human associated bacteria and fungi were performed as described in the NCCLS manual. Unless otherwise noted, the majority of the bacteria isolates tested were obtained from the ATCC. The assays were performed in sterile 96 well plates, and the total volume per well was 100 microliters. The bacterial inoculum was prepared to yield approximately $10^4$ to $10^5$ colony forming units per well and the compounds were tested at concentrations from 0.0625 to 64 micrograms/ml in two-fold step dilution. The actual colony forming units per well was confirmed by plating onto Mueller-Hinton or blood agar. Two wells were inoculated for a given concentration. The plates were incubated for 16 to 20 hours at 35° C. unless otherwise specified with or without 5% $CO_2$. The MIC (minimum inhibitory concentration) was defined as that concentration of compound resulting in no visible growth of the test organism. The MIC (minimum inhibitory concentration in each test) was determined by visually observing the plates following incubation. All Bacillus anthracis testing was conducted in a bio-safety Level 3 facility.

Kakadumycin A was tested on a comparative basis (MIC's) with commercial preparations of echinomycin and vancomycin. Generally, kakadumycin A was active against a wide range of Gram positive bacteria and its activity generally exceeded that of echinomycin by one dilution point, i.e., twice as active (Table 15). The most noted exception to this was the response of a number of Bacillus anthracis isolates to both compounds with Bacillus anthracis being much more sensitive to kakadumycin A than echinomycin, ca. 3 dilutions or a potency of ca. of 4-5 times (Table 15). However, in the cases of Enterococcus faecium, Staphylococcus simulans, Staphylococcus aureus and Listeria monocytogenes, the responses to both compounds were virtually identical. Both kakadumycin A and echinomycin were as or more potent than vancomycin against all bacteria tested.

TABLE 15

Comparative MIC's of echinomycin and kakadumycin A and vancomycin against various human-associated pathogenic bacteria.

| Organism | Kakadumycin A micrograms/ml | Echinomycin micrograms/ml | Vancomycin micrograms/ml |
|---|---|---|---|
| Bacillus anthracis* 40/BA 100 | 0.3 | 1.4 | N.D. |
| Bacillus anthracis* 14578 | 0.55 | 1.99 | N.D. |
| Bacillus anthracis 28 | 0.43 | 2.4 | N.D |
| Bacillus anthracis 62-8 | 0.41 | 1.4 | N.D. |
| Staphylococcus simulans ATCC 11631 | 0.25 | 0.25 | 1.0 |
| Enterococcus faecalis ATCC 29212 | 0.062 | 0.125 | 2.0 |
| Enterococcus faecalis VRE, ATCC 51299 | 0.062 | 0.125 | 4.0 |
| Enterococcus faecium ATCC 49624 | 0.062 | <=0.062 | 0.5 |
| Listeria monocytogenes ATCC 19114 | 0.25 | 0.5 | 1.0 |
| Listeria monocytogenes ATCC 19115 | 0.25 | 0.25 | 1.0 |
| Shigella dysenteriae ATCC 11835 | 4.0 | 8.0 | 2.0 |
| Staphylococcus epidermidis ATCC 12228 | 0.125 | 0.25 | 1.0 |
| Staphylococcus aureus ATCC 29213 | 0.25 | 0.5 | 1.0 |
| Staphylococcus aureus MRSA, ATCC 33591 | 0.5 | 0.5 | 2.0 |
| Staphylococcus aureus GISA, ATCC 700787 | 0.5 | 1.0 | 8.0 |
| Staphylococcus aureus ATCC 27734 | 0.125 | 0.25 | 1.0 |

TABLE 15-continued

Comparative MIC's of echinomycin and kakadumycin A and vancomycin against various human-associated pathogenic bacteria.

| Organism | Kakadumycin A micrograms/ml | Echinomycin micrograms/ml | Vancomycin micrograms/ml |
|---|---|---|---|
| *Streptococcus pneumoniae* ATCC 49619 | <0.0325 | <0.0325 | 0.125 |
| *Streptococcus pneumoniae* ATCC 70674 | <0.0325 | <0.0325 | 0.25 |
| *Streptococcus pneumoniae* ATCC 70676 | <0.0325 | <0.0325 | 0.25 |

*All *Bacillus anthracis* isolates are listed according to the original numerical designations given to them in the literature and each is stored in the BYU microbiological collection. Most *Bacillus anthracis* isolates are sensitive to ciprofloxacin at ca. 0.1 micrograms/ml.
N.D. = not determined Cultures of *Plasmodium falciparum* strain CSC-1 (Honduras) were maintained according to previously published methods (Trager and Jensen, 1976; Trager and Jensen, 1978) except that human serum was replaced with Albumax I (Gibco, BRL); 6% w/v stock solution in RPMI 1640 medium containing 0.1 mg/ml hypoxanthine stored at −20° C. All cultures were maintained in a microaerophilic environment containing 1% oxygen/5% $CO_2$ with the balance being nitrogen. The stock solution was diluted at a ratio of 5:100 v/v of RPMI 1640 to give a final concentration of 0.3% Albumax I. Stock solutions of the compounds to be tested, including kakadumycin A, echinomycin, and chloroquine, were initially dissolved in methanol and diluted to final concentrations in Albumax-supplemented RPMI 1640. Control cultures contained the same quantity of methanol or water as that used in the experimental trials. All other specific details of the assay especially the use of the labeled phenylalanine and the Giemsa staining procedures are found in a recent publication (Castillo et al., 2002). Data are reported as $IC_{50}$ values (Castillo et al., 2002).

Comparative tests with the malarial parasite *Plasmodium falciparum* showed that echinomycin produced an $IC_{50}$ of 4.08±0.1 ng/ml whereas kakadumycin A yielded an $IC_{50}$ of 7.04±0.12 ng/ml. This was the only case, in all of the anti-infectious tests conducted, in which echinomycin was more active than kakadumycin A. Tests against a primary human cell line, human mammary epithelial cells (Clonetics, Walkersville, Md.), showed that both compounds displayed cytotoxicity with $IC_{50}$'s of 4.8+1.1 and 8.0±1.4 micrograms/ml for echinomycin and kakadumycin A, respectively. Furthermore, both compounds were active against the human breast cancer cell line BT 20 with $IC_{50}$'s of 6.5 and 4.5 ng/ml for echnimonycin and kakadumycin A, respectively.

Example 19

Antimalarial Testing of Kakadumycin A

Kakadumycin A was tested for antimalarial activity according to Example 8. Stock solutions of the compounds to be tested, including kakadumycin A, echinomycin, and chloroquine, were initially dissolved in methanol and diluted to final concentrations in Albumax-supplemented RPMI 1640. Control cultures contained the same quantity of methanol or water as that used in the experimental trials. All other specific details of the assay especially the use of the labeled phenylalanine and the Giemsa staining procedures are found in a recent publication (Castillo et al., 2002). Data were reported as $IC_{50}$ values (Castillo et al., 2002).

Comparative tests with the malarial parasite *Plasmodium falciparum* showed that echinomycin produced an $IC_{50}$ of 4.08±0.1 ng/ml whereas kakadumycin A yielded an $IC_{50}$ of 7.04±0.12 ng/ml. This was the only case, in all of the anti-infectious tests conducted, in which echinomycin was more active than kakadumycin A. Tests against a primary human cell line, human mammary epithelial cells (Clonetics, Walkersville, Md.), showed that both compounds displayed cytotoxicity with $IC_{50}$'s of 4.8±1.1 and 8.0±1.4 micrograms/ml for echinomycin and kakadumycin A, respectively. Furthermore, both compounds were active against the human breast cancer cell line BT 20 with $IC_{50}$'s of 6.5 and 4.5 ng/ml for echnimonycin and kakadumycin A, respectively.

Example 20

Macromolecular Synthesis Whole Cell Assays—Mode of Action of Kakadumycin A and Munumbicin B The mechanistic action of kakadumycin A, and munumbicin B was determined by measuring the incorporation of the appropriate radiolabeled macromolecular synthesis precursor into trichloroacetic acid (TCA)-precipitated material from antibiotic-treated *Bacillus subtilis* cultures (Selva et al., 1991; Singh et al., 2000). ATCC medium 21 was used for *Bacillus subtilis* macromolecular synthesis studies. The medium was composed per liter of 0.5 g of $K_2HPO_4$, 0.5 g of ferric ammonium citrate, 0.5 g of $MgSO_4.7H_2O$, 2% glycerol, 2 g of citric acid, and 4 g of glutamic acid per liter; pH 7.4.

[Methyl-$^3$H]thymidine (TRK686; 90 Ci/mmol), [5,6-$^3$H] uridine (TRK410; 41 Ci/mmol), [$^3$H]amino acid mixture (TRK550; a mixture of leucine, lysine, phenylalanine, proline, and tyrosine, with specific activities of 161, 80, 125, 101, 96 Ci/mmol, respectively), and N-acetyl-D-[1-$^3$H]glucosamine (TRK376; 11 Ci/mmol) were obtained from Amersham Pharmacia Biotech (Piscataway, N.J.).

Overnight cultures of *Bacillus subtilis* 1A757 (*Bacillus* Genetic Stock Center, Columbus, Ohio) were diluted 1:100 in ATCC medium 21 and incubated at 37° C. and 200 rpm until $A_{600}$ of 0.1. Aliquots of 2 ml cultures were then transferred to several 14 ml polypropylene Falcon tubes. To the aliquots kakadumycin A (0.125 micrograms/ml), munumbicin B (2 micrograms/ml), echinomycin (0.25 micrograms/ml), ciprofloxacin (0.125 micrograms/ml), rifampin (0.25 micrograms/ml), chloramphenicol (4 micrograms/ml), or vancomycin (0.25 micrograms/ml) were added. No drug control cultures were included in each experiment. The concentrations of antibiotics used were 1×MIC against *Bacillus subtilis*. Ciprofloxacin, rifampin, chloramphenicol, or vancomycin was used as positive controls for inhibitory mechanism for DNA, RNA, protein, or cell wall synthesis, respectively. A volume of 0.1 ml culture was taken at 0 (before drug addition), 5, 10, 20, and 30 minutes post-drug treatment, and added to a tube containing one of the following radiolabeled precursors: DNA (2 micro-Ci/ml [$^3$H]thymidine), RNA (2 micro-Ci/ml [$^3$H]uridine with 0.00035 micrograms unlabeled uridine per ml), protein (2 micro-Ci/ml [$^3$H]amino acid mixture with 0.035 micrograms each of unlabeled leucine, lysine, phenylalanine, proline, and tyrosine per ml), or cell wall (2 micro-Ci/ml [$^3$H]N-acetylglucosamine with 3.5 micrograms unlabeled N-acetylglucosamine per ml), and pulse-labeled at 37° C. for 5 minutes. The macromolecular materials were then precipitated by adding 1 ml of cold 10% TCA and incubated on ice for at least 1 hour. The precipitated materials were collected kinetics, and had no effect on DNA synthesis. Kakadumycin A shared nearly identical profiles with echinomycin in four macromolecular synthesis assays, indicating that they may possess the same mode of action (FIG. 21). The results indicated that kakadumycin A preferentially inhibited RNA synthesis, and may share the same mode of action as echinomycin, which inhibits RNA synthesis by binding to DNA template (Sato et al., 1967). Munumbicin B showed some inhibitory effect on RNA and cell wall syntheses, and milder inhibitory effect on protein synthesis, while no effect on DNA synthesis. Munumbicin B reached minimal inhibition of cell wall synthesis at 20 minutes, but became less inhibitory at 30 and 60 minutes. Acceleration of DNA synthesis rate was observed at 60 minutes in munumbicin B-treated culture.

TABLE 16

Effect of antibiotics on incorporation of radiolabeled precursors of DNA, RNA, protein, and cell wall in *Bacillus subtilis*

| Compound | % [$^3$H]thymidine (DNA synthesis) | | % [$^3$H]uridine (RNA synthesis) | | % [$^3$H]amino acid mixture (Protein synthesis) | | % [$^3$H]N-acetyl glucosamine (Cell wall synthesis) | |
|---|---|---|---|---|---|---|---|---|
| | 5 min | 10 min | 5 min | 10 min | 5 min | 10 min | 5 min | 10 min |
| Kakadumycin A | 96 | 112 | 42 | 38 | 71 | 53 | 65 | 55 |
| Munumbicin B | 93 | 102 | 64 | 59 | 85 | 74 | 81 | 59 |
| Echinomycin | 1 | 11 | 41 | 37 | 73 | 62 | □ | □ |
| Ciprofloxacin | 36 | 35 | □ | □ | □ | □ | □ | □ |
| Rifampin | □ | □ | 13 | 15 | □ | — | 47 | 48 |
| Chloramphenicol | 58 | 44 | □ | □ | 44 | 36 | □ | □ |
| Vancomycin | □ | □ | □ | □ | □ | □ | 33 | 41 |

1. Exponential-phase cells were treated with antibiotics for indicated time and were pulse-labeled for 5 minutes. Shown is % incorporation of that of the untreated culture. Each data is repeated at least twice.
2.—: Not determined.

on GF/C glass fiber filters, followed by washing with 5 ml of chilled 5% TCA and 5 ml of chilled absolute ethanol. The filters were air-dried, and placed into vials containing 3 ml of scintillation cocktail before measuring the radioactivity in a liquid scintillation counter (Wallac 1409, PerkinElmer, Los Angeles, Calif.). The levels of incorporation were expressed as the percentage of the untreated control.

Effects of kakadumycin A and munumbicin B on macromolecular synthesis was determined in *Bacillus subtilis*. Inhibition of DNA, RNA, protein, and cell wall synthesis was determined by measuring incorporation of $^3$H-labeled thymidine, uridine, amino acid mixture, or N-acetylglucosamine, respectively, into the TCA-precipitable material from *Bacillus subtilis* cultures. Effect of kakadumycin A and munumbicin B on macromolecular syntheses was measured as percent precursor incorporation in drug-treated samples compared to that of the untreated cultures. Echinomycin, a quinoxaline, and other macromolecular syntheses inhibitors (ciprofloxacin, rifampin, chloramphenicol, and vancomycin for DNA, RNA, protein, cell wall synthesis inhibitors, respectively) were used as controls.

The RNA synthesis rate was significantly inhibited by kakadumycin A (Table 16). Kakadumycin A inhibited protein and cell wall syntheses to a lesser extent and at slower MICs were determined against *Bacillus subtilis* and *Staphylococcus aureus* in the presence of double stranded DNA to determine if DNA inhibits the antimicrobial activity of kakadumycin A, munumbicin B, and munumbicin C, which had been previously shown for echinomycin. The effect of the addition of DNA on MICs was determined by adding 20 micrograms per well of sheared salmon sperm DNA. The MICs for both kakadumycin A and echinomycin were increased by 30-fold or higher when DNA was added (Table 17). In contrast, the MICs for vancomycin, a cell wall inhibitor, were not affected by the addition of DNA. The increase in MICs when DNA is added suggested that kakadumycin A binds DNA and may inhibit RNA synthesis by a mechanism similar to echinomycin. The results indicated that kakadumycin A preferentially inhibited RNA synthesis, and may share the same mode of action as echinomycin, which inhibits RNA synthesis by binding to DNA template (Sato et al., 1967). Munumbicin B inhibited RNA and cell wall syntheses, and also inhibited protein synthesis to a lesser extent. The MICs of munumbicin B and munumbicin C are both affected by the addition of double stranded DNA.

TABLE 17

MIC's (micrograms/ml) of kakadumycin A, echinomycin, and vancomycin in the presence of double stranded DNA.

| | Kakadumycin A | | Echinomycin | | Munumbicin B | | Munumbicin C | | Vancomycin | |
|---|---|---|---|---|---|---|---|---|---|---|
| DNA | − | + | − | + | − | + | − | + | − | + |
| B. subtilis 1A757 | 0.0625 | 4 | 0.125 | 8 | 1 to 2 | >32 | 0.5 | >32 | 0.125 | 0.125 |
| S. aureus ATCC 6583P | 0.25 | 16 | 0.5 | 16 | 2 | >32 | 0.5 | >32 | 0.5 | 0.5 |

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| Streptomyces munumbi | NRRL 30562 | Mar. 7, 2002 |
| Streptomyces sp. | NRRL 30563 | Mar. 12, 2002 |
| Streptomyces sp. | NRRL 30564 | Mar. 12, 2002 |
| Streptomyces sp. | NRRL 30565 | Mar. 12, 2002 |
| Streptomyces sp. | NRRL 30566 | Mar. 7, 2002 |
| Streptomyces sp. | NRRL 30567 | Mar. 12, 2002 |

The strains have been deposited under conditions that assure that access to the cultures will be available during the pendency of this patent application to one determined by the Commissioner of Patents and Trademarks to be entitled thereto under 37 C.F.R. § 1.14 and 35 U.S.C. § 122. The deposits represent substantially pure cultures of the deposited strains. The deposits are available as required by foreign patent laws in countries wherein counterparts of the subject application, or its progeny are filed. All restrictions on the availability to the public of the material so deposited will be irrevocably removed upon the granting of a patent. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated strain of a *Streptomyces* spp. which is an endophyte of a *Kennedia nigriscans* plant stem, wherein the strain is *Streptomyces munumbi* NRRL 30562.

2. The isolated strain of *Streptomyces munumbi* NRRL 30562, which is selected by a method comprising steps of:
   (a) culturing tissue from the interior region of a *Kennedia nigriscans* plant stem on nutrient media for a time sufficient to permit colony formation by a strain of endophytic *Streptomyces munumbi* NRRL 30562 associated with the tissue; and
   (b) selecting the *Streptomyces munumbi* NRRL 30562 strain.

3. A composition comprising a suitable carrier and the strain of claim 1.

4. A composition comprising the strain of claim 1 affixed to a substrate.

5. A composition comprising a suitable carrier and the strain of claim 2.

6. A composition comprising the strain of claim 2 affixed to a substrate.

* * * * *